(12) United States Patent
Dehmlow et al.

(10) Patent No.: US 8,063,088 B2
(45) Date of Patent: Nov. 22, 2011

(54) IMIDAZOLIDINE DERIVATIVES

(75) Inventors: Henrietta Dehmlow, Loerrach (DE); Ulrike Obst Sander, Reinach BL (CH); Tanja Schulz-Gasch, Liestal (CH); Matthew Wright, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 109 days.

(21) Appl. No.: 12/477,943

(22) Filed: Jun. 4, 2009

(65) Prior Publication Data
US 2009/0312382 A1 Dec. 17, 2009

(30) Foreign Application Priority Data
Jun. 11, 2008 (EP) ..................................... 08158075

(51) Int. Cl.
*A61K 31/415* (2006.01)
*A01N 43/50* (2006.01)
(52) U.S. Cl. ....................................................... 514/392
(58) Field of Classification Search ........................ None
See application file for complete search history.

(56) References Cited

U.S. PATENT DOCUMENTS
2006/0040999 A1 2/2006 Ali et al.
2006/0074103 A1 4/2006 Corte et al.

FOREIGN PATENT DOCUMENTS
WO WO 03/099769 12/2003

OTHER PUBLICATIONS

Anderson (Chem and Biol 10:787-797, 2003).*
Thiel (Nature Biotechnol 2:513-519, 2004).*
Willy et al., Genes Dev., 9, pp. 1033-1045 (1995).
Song et al., Proc. Natl. Acad. Sci. USA., 91, pp. 10809-10813 (1994).
Geyeregger et al., Cell. Mol. Life. Sci., 63, pp. 524-539 (2006).
Miller, N.E., Lipids, 13, pp. 914-919 (1978).
Forrester et al., Am. J. Cardiol., 98, pp. 1542-1549 (2006).
Gordon et al., Am. J. Med., 62, pp. 707-714 (1977).
Lund et al., Arterioscler. Thromb. Vasc. Biol., 23, pp. 1169-1177 (2003).
Mitro et al., Nature, 445, pp. 219-223 (2007).
Joseph et al., Curr. Opin. Pharmacol., 3, pp. 192-197 (2003).
Cao et al., J. Biol. Chem., 278, pp. 1131-1136 (2003).
Ando et al., Tetrahedron, 54, pp. 13485-13494 (1998).
Bull et al., J. Chem. Soc., Perkin Trans., 1, pp. 3106-3111 (2001).
Barr et al., J. Chem. Soc., pp. 438-441 (1945).
Bennet D. J. et al, *Expert Opinion on Therapeutic Patents*, 16:12 (2006) 1673-1699 XP002500308.
Bennet D. J. et al, *Current Medicinal Chemistry*, (2008) 15, 195-209 XP002540630.

* cited by examiner

*Primary Examiner* — Brandon Fetterolf
*Assistant Examiner* — Craig Ricci
(74) *Attorney, Agent, or Firm* — George W. Johnston; Patricia S. Rocha-Tramaloni; Gene J. Yao

(57) ABSTRACT

The invention is concerned with novel imidazolidine derivatives of formula (I)

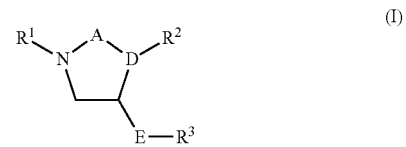

wherein $R^1$ to $R^3$, A, D and E are as defined in the description and in the claims, as well as physiologically acceptable salts and esters thereof. These compounds bind to LXR alpha and LXR beta and can be used as medicaments.

15 Claims, No Drawings

IMIDAZOLIDINE DERIVATIVES

PRIORITY TO RELATED APPLICATION(S)

This application claims the benefit of European Patent Application No. 08158075.5, filed Jun. 11, 2008, which is hereby incorporated by reference in its entirety.

FIELD OF THE INVENTION

The present invention is directed to, for example, novel imidazolidine derivatives, their manufacture and their use as medicaments. In particular, the present invention provides the novel compounds of formula (I), which bind to LXR alpha and/or LXR beta and pharmaceutically acceptable compositions thereof.

BACKGROUND OF THE INVENTION

Liver-X-Receptors (LXRs) are members of the nuclear hormone receptor superfamily. The LXRs are activated by endogenous oxysterols and glucose and regulate the transcription of genes controlling multiple metabolic pathways. Two subtypes, LXR alpha and LXR beta, have been described (Willy, P. J. et al., Genes Dev. 1995, 9:1033-45; Song, C. et al., Proc Natl Acad Sci USA. 1994, 91:10809-13). LXR beta is ubiquitously expressed, while LXR alpha is predominantly expressed in cholesterol metabolizing tissues such as the liver, adipose, intestine and macrophage. The LXRs modulate a variety of physiological responses including regulation of cholesterol absorption, cholesterol elimination (bile acid synthesis), and transport of cholesterol from peripheral tissues via plasma lipoproteins to the liver. The LXRs also appear to regulate genes involved in glucose metabolism, cholesterol metabolism in the brain, cellular differentiation and apoptosis, inflammation, and infectious diseases (Geyeregger, R. et al., Cell. Mol. Life. Sci. 2006, 63:524-539).

About half of all patients with coronary artery disease have low concentrations of plasma high-density lipoprotein cholesterol (HDL-C). The atheroprotective function of HDL was first highlighted almost 25 years ago and stimulated exploration of the genetic and environmental factors that influence HDL-C levels (Miller N E., Lipids 1978, 13:914-9). The protective function of HDL derives from its role in a process termed reverse cholesterol transport (Forrester, J. S. and Shah, P. K., Am. J. Cardiol. 2006, 98:1542-49). HDL mediates the removal of cholesterol from cells in peripheral tissues, including macrophage foam cells in the atherosclerotic lesions of the arterial wall. HDL delivers its cholesterol to the liver and sterol-metabolizing organs for conversion to bile and elimination in feces. Studies have shown that HDL-C levels are predictive of coronary artery disease risk independently of low-density lipoprotein cholesterol (LDL-C) levels (Gordon, T. et al., Am J. Med. 1977, 62:707-14).

At present, the estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial unfavorable side-effects limit the therapeutic potential of this approach.

It has been observed that as many as 90% of the 14 million diagnosed type 2 diabetic patients in the United States are overweight or obese, and a high proportion of type 2 diabetic patients have abnormal concentrations of lipoproteins. Studies have shown that the prevalence of total cholesterol>240 mg/dl is 37% in diabetic men and 44% in women. The rates for LDL-C>160 mg/dl are 31% and 44%, and for HDL-C<35 mg/dl are 28% and 11%, in diabetic men and women respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and has been shown to afflict 80-90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in the later stages of the disease, due to exhaustion and failure of pancreatic insulin-producing capacity. Thus, T2D is a cardiovascular-metabolic syndrome associated with multiple co-morbidities, including insulin resistance, dyslipidemia, hypertension, endothelial dysfunction and inflammatory atherosclerosis.

The first line of treatment for dyslipidemia and diabetes at present generally involves a low-fat and low-glucose diet, exercise and weight loss. However, compliance can be moderate, and as the disease progresses, treatment of the various metabolic deficiencies becomes necessary with lipid-modulating agents such as statins and fibrates for dyslipidemia, and hypoglycemic drugs, e.g. sulfonylureas, metformin, or insulin sensitizers of the thiazolidinedione (TZD) class of PPARγ-agonists, for insulin resistance. Recent studies provide evidence that modulators of LXRs they result in compounds with enhanced therapeutic potential, and as such, modulators of LXRs should improve the plasma lipid profile, and raise HDL-C levels (Lund, E. G. et al., Arterioscler. Thromb. Vasc. Biol. 2003, 23:1169-77; Mitro, N. et al., Nature 2007, 445: 219-23). LXRs are also known to control the efflux of cholesterol from the macrophage foam cell of the atherosclerotic lesion, and agonists of LXRs have been shown to be atheroprotective (Joseph, S. B. and Tontonoz, P., Curr. Opin. Pharmacol. 2003, 3:192-7). Thus, modulators of LXRs may be effective treatments for the atherosclerotic disease which underlies the cardiovascular morbidity and mortality of stroke and heart disease. Recent observations also suggest that there is an independent LXR mediated effect on insulin-sensitization in addition to its role in atheroprotection (Cao, G. et al., J Biol. Chem. 2003, 278:1131-6). Thus LXR modulators may also show superior therapeutic efficacy on HDL-raising and atheroprotection, with additional effects on diabetes, compared to current therapies.

While compounds that bind to and activate LXR alpha and LXR beta have previously been suggested (e.g.: WO 03/099769 the present invention provides the novel compounds of formula (I), which bind to LXR alpha and/or LXR beta, and unexpectedly exhibit improved pharmacological properties compared to the compounds known in the art, concerning e.g. metabolic stability, selectivity, bioavailability and activity.

SUMMARY OF THE INVENTION

The invention is concerned with novel imidazolidine derivatives of the formula (I)

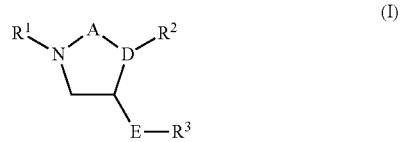

wherein

A is —C(O)—, —CH$_2$—C(O)—, —C(O)—CH$_2$— or —CH$_2$—CH$_2$—;

D is N or CH;

E is arylene which can optionally be substituted with 1 to 4 substituents independently selected from the group consisting of halogen, lower-alkyl and fluoro-lower-alkyl;

R$^1$ is lower-alkyl-O—C(O) or R$^4$—SO$_2$;

R$^2$ is lower-alkyl or aryl, wherein aryl can optionally be substituted with 1 to 4 substituents independently selected from the group consisting of halogen, lower-allyl, lower-alkoxy, fluoro-lower-alkyl and fluoro-lower-alkoxy;

R$^3$ is aryl or heteroaryl, wherein aryl or heteroaryl can optionally be substituted with 1 to 4 substituents independently selected from the group consisting of halogen, lower-alkyl, lower-alkoxy, fluoro-lower-alkyl, fluoro-lower-alkoxy, COOH, lower-alkyl-SO$_2$, lower-alkyl-SO$_2$—NH, lower-alkyl-SO$_2$—N(lower-alkyl), COOH-lower-alkyl, hydroxy-lower-alkyl, NH$_2$-lower-alkyl, N(H,lower-alkyl)-lower-alkyl, N(lower-alkyl)-2-lower-alkyl, NO$_2$, CN, NH$_2$—SO$_2$, N(H,lower-alkyl)-SO$_2$, N(lower-alkyl)$_2$-SO$_2$, lower-alkyl-NH—SO$_2$ and lower-alkyl-N(lower-alkyl)-SO$_2$;

R$^4$ is lower-alkyl, aryl or heteroaryl, wherein aryl or heteroaryl can optionally be substituted with 1 to 4 substituents independently selected from the group consisting of halogen, lower-alkyl, lower-alkoxy, fluoro-lower-alkyl and fluoro-lower-alkoxy;

and pharmaceutically acceptable salts and esters thereof.

Further, the invention is concerned with a process for the manufacture of the above compounds, pharmaceutical preparations which contain such compounds as well as the use of these compounds for the production of pharmaceutical preparations.

DETAILED DESCRIPTION OF THE INVENTION

The novel compounds of the present invention have been found to bind to and selectively activate LXR alpha and/or LXR beta or coactivate LXR alpha and LXR beta. Consequently, cholesterol absorption is reduced, HDL cholesterol is increased, and inflammatory atherosclerosis is reduced. Since multiple facets of combined dyslipidemia and cholesterol homeostasis are addressed by LXR modulators, novel compounds of the present invention have an enhanced therapeutic potential compared to the compounds already known in the art.

A. Definitions

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

Lower-alkyl groups can optionally be substituted, e.g. by hydroxy. Such groups are referred to as "hydroxy-lower-alkyl". Examples of hydroxy-lower-alkyl groups are e.g. hydroxymethyl, hydroxyethyl, hydroxypropyl or hydroxybutyl groups, preferably hydroxyethyl. The term "fluoro-lower-alkyl" refers to lower-alkyl groups which are mono- or multiply substituted with fluorine. Examples of fluoro-lower-alkyl groups are e.g. CFH$_2$, CF$_2$H, CF$_3$, CF$_3$CH$_2$, CF$_3$(CH$_2$)$_2$, (CF$_3$)$_2$CH and CF$_2$H—CF$_2$.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —NH$_2$, methylamino, ethylamino, dimethylamino, diethylamino, methyl-ethylamino, pyrrolidin-1-yl or piperidino etc.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl. Cycloalkyl groups can optionally be substituted as described below in the description and claims.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"-O—, wherein R" is fluoro-lower-alkyl. Examples of fluoro-lower-alkoxy groups are e.g. CFH$_2$—O, CF$_2$H—O, CF$_3$—O, CF$_3$CH$_2$—O, CF$_3$(CH$_2$)$_2$—O, (CF$_3$)$_2$CH-O, and CF$_2$H—CF$_2$—O.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups.

The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "aryl", alone or in combination, relates to the phenyl or naphthyl group, preferably the phenyl group, which can optionally be substituted by 1 to 5, preferably 1 to 3, substituents independently selected from the group consisting of lower-alkyl, lower-alkoxy, halogen, hydroxy, CN, CF$_3$, amino, aminocarbonyl, carboxy, NO$_2$, dioxo-lower-alkylene (forming e.g. a benzodioxyl group), lower-alkylsulfonyl, aminosulfonyl, lower-alkylcarbonyl, lower-alkylcarbonyloxy, lower-alkylcarbonyl-NH, lower-alkoxycarbonyl, fluoro-lower-alkyl, fluoro-lower-alkoxy, lower-alkoxy-lower-alkyl, cycloalkyl and phenyloxy. Unless stated otherwise, preferred substituents are halogen, lower-alkyl, fluoro-lower-alkyl, lower-alkoxy and fluoro-lower-alkoxy. Furthermore, aryl groups can preferably be substituted as described below in the description and claims.

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furanyl, pyridinyl, pyridazinyl, pyrimidinyl, pyrazinyl, thiophenyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, benzoisothiazolyl, benzoxazolyl, benzoisoxazolyl, 3-thieno[3,2-c]pyridin-4-yl and quinolinyl. Preferred heteroaryl groups are isoxazolyl and pyridinyl. A heteroaryl group may optionally have a substitution pattern as described earlier in connection with the term "aryl". Furthermore, heteroaryl groups can preferably be substituted as described below in the description and claims.

The term "arylene" refers to a divalent aryl as defined above.

Compounds of formula (I) may form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid, or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) may further form salts with bases. Examples of such salts are alkaline, earth-alkaline and ammonium salts such as e.g. Na—, K—, Ca— and trimethylammonium salt. The term "pharmaceutically acceptable salts" also refers to such salts.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

All references referred to herein are hereby incorporated by reference in their entirety.

B. Detailed Description

In detail, the present invention relates to compounds of formula (I)

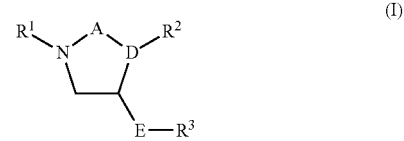

wherein
A is —C(O)—, —CH$_2$—C(O)—, —C(O)—CH$_2$— or —CH$_2$—CH$_2$—;
D is N or CH;
E is arylene which can optionally be substituted with 1 to 4 substituents independently selected from the group consisting of halogen, lower-alkyl and fluoro-lower-alkyl;
R$^1$ is lower-alkyl-O—C(O) or R$^4$—SO$_2$;
R$^2$ is lower-alkyl or aryl, wherein aryl can optionally be substituted with 1 to 4 substituents independently selected from the group consisting of halogen, lower-alkyl, lower-alkoxy, fluoro-lower-alkyl and fluoro-lower-alkoxy;
R$^3$ is aryl or heteroaryl, wherein aryl or heteroaryl can optionally be substituted with 1 to 4 substituents independently selected from the group consisting of halogen, lower-alkyl, lower-alkoxy, fluoro-lower-alkyl, fluoro-lower-alkoxy, COOH, lower-alkyl-SO$_2$, lower-alkyl-SO$_2$—NH, lower-alkyl-SO$_2$—N(lower-alkyl), COOH-lower-alkyl, hydroxy-lower-alkyl, NH$_2$-lower-alkyl, N(H,lower-alkyl)-lower-alkyl, N(lower-alkyl)-2-lower-alkyl, NO$_2$, CN, NH$_2$—SO$_2$, N(H,lower-alkyl)-SO$_2$, N(lower-alkyl)$_2$-SO$_2$, lower-alkyl-NH—SO$_2$ and lower-alkyl-N(lower-alkyl)-SO$_2$;
R$^4$ is lower-alkyl, aryl or heteroaryl, wherein aryl or heteroaryl can optionally be substituted with 1 to 4 substituents independently selected from the group consisting of halogen, lower-alkyl, lower-alkoxy, fluoro-lower-alkyl and fluoro-lower-alkoxy;
and pharmaceutically acceptable salts and esters thereof.

Compounds of formula (I) are individually preferred, pharmaceutically acceptable salts thereof are individually preferred and pharmaceutically acceptable esters thereof are individually preferred, with the compounds of formula (I) being particularly preferred.

The compounds of formula (I) have one or more asymmetric C atoms and can therefore exist as an enantiomeric mixture, mixture of stereoisomers or as optically pure compounds.

Preferred compounds according to the present invention are those, wherein A is —C(O)—, —CH$_2$—CH$_2$— or —C(O)—CH$_2$—. Each of the groups —C(O)—, —CH$_2$—CH$_2$— or —C(O)—CH$_2$— individually represents a separate preferred embodiment.

Other preferred compounds are those, wherein D is N. Furthermore, it is preferred that D is CH. Another preferred embodiment is concerned with compound as defined above, wherein E is phenylene, preferably 1,3-phenylene or 1,4-phenylene. More preferably E is 1,3-phenylene.

Furthermore, it is preferred that R$^1$ is lower-alkyl-O—C(O). More preferably, R$^1$ is (CH$_3$)$_3$C—O—C(O). In addition, compounds wherein R$^1$ is R$^4$—SO$_2$ and R$^4$ is as defined above are also preferred.

Another preferred embodiment of the present invention is concerned with compounds as defined above, wherein $R^2$ is lower-alkyl or phenyl, which phenyl can optionally be substituted with 1 to 2 substituents independently selected from lower-alkyl. More preferably, $R^2$ isopropyl, phenyl or 2-methyl-phenyl.

Other preferred compounds of the present invention are those, wherein $R^3$ is phenyl or pyridinyl, which phenyl or pyridinyl can optionally be substituted with 1 to 3 substituents independently selected from the group consisting of halogen, lower-alkyl, lower-alkoxy, COOH, lower-alkyl-$SO_2$, lower-alkyl-$SO_2$—NH, COOH-lower-alkyl, hydroxy-lower-alkyl, $NH_2$-lower-alkyl, $NO_2$, CN, $NH_2$—$SO_2$ and N(H,lower-alkyl)-$SO_2$. More preferably, $R^3$ is phenyl or pyridinyl, which phenyl or pyridinyl can optionally be substituted with 1 to 2 substituents independently selected from the group consisting of lower-alkyl-$SO_2$, hydroxy-lower-alkyl, $NH_2$-lower-alkyl and $NH_2$—$SO_2$. Even more preferably, $R^3$ is 3-methanesulfonyl-phenyl, 4-hydroxymethyl-3-methanesulfonyl-phenyl, 3-sulfamoyl-phenyl, 5-methanesulfonyl-pyridin-3-yl or 3-aminomethyl-phenyl.

Other preferred compounds of the present invention are those, wherein $R^4$ is lower-alkyl, phenyl or isoxazolyl, which phenyl or isoxazolyl can optionally be substituted with 1 to 2 substituents independently selected from the group consisting of halogen and lower-alkyl. Preferably, $R^4$ is lower-alkyl or phenyl, which phenyl can optionally be substituted with halogen. More preferably, $R^4$ is ethyl, isopropyl, phenyl or 2-fluoro-phenyl.

In particular, preferred compounds are the compounds of formula (I) described in the examples as individual compounds as well as pharmaceutically acceptable salts and esters thereof.

Preferred compounds of formula (I) are those selected from the group consisting of
4'-(1-Benzenesulfonyl-2-oxo-3-phenyl-imidazolidin-4-yl)-biphenyl-4-carboxylic acid,
4'-(1-Benzenesulfonyl-2-oxo-3-phenyl-imidazolidin-4-yl)-biphenyl-3-carboxylic acid,
1-Benzenesulfonyl-4-(2',5'-dimethyl-biphenyl-4-yl)-3-phenyl-imidazolidin-2-one,
1-Benzenesulfonyl-4-(3'-methanesulfonyl-biphenyl-4-yl)-3-phenyl-imidazolidin-2-one,
3'-(1-Benzenesulfonyl-2-oxo-3-phenyl-imidazolidin-4-yl)-biphenyl-4-carboxylic acid,
3'-(1-Benzenesulfonyl-2-oxo-3-phenyl-imidazolidin-4-yl)-biphenyl-3-carboxylic acid,
1-Benzenesulfonyl-4-(3'-methanesulfonyl-biphenyl-3-yl)-3-phenyl-imidazolidin-2-one,
N-[3'-(1-Benzenesulfonyl-2-oxo-3-phenyl-imidazolidin-4-yl)-biphenyl-3-yl]-methanesulfonamide,
N-[4'-(1-Benzenesulfonyl-2-oxo-3-phenyl-imidazolidin-4-yl)-biphenyl-3-yl]-methanesulfonamide,
3-[3'-(1-Benzenesulfonyl-2-oxo-3-phenyl-imidazolidin-4-yl)-biphenyl-4-yl]-propionic acid,
3'-(1-Benzenesulfonyl-2-oxo-3-phenyl-imidazolidin-4-yl)-biphenyl-2-carboxylic acid,
(RS)-1-Benzenesulfonyl-3-isopropyl-4-(3'-methanesulfonyl-biphenyl-3-yl)-imidazolidin-2-one,
3-Isopropyl-4-(3'-methanesulfonyl-biphenyl-3-yl)-1-(propane-2-sulfonyl)-imidazolidin-2-one,
1-(2-Fluoro-benzenesulfonyl)-3-isopropyl-4-(3'-methanesulfonyl-biphenyl-3-yl)-imidazolidin-2-one,
3-Isopropyl-4-(3'-methanesulfonyl-biphenyl-3-yl)-1-(5-methyl-isoxazole-4-sulfonyl)-imidazolidin-2-one,
1-Benzenesulfonyl-4-(4'-hydroxymethyl-3'-methanesulfonyl-biphenyl-3-yl)-3-phenyl-imidazolidin-2-one,
3-Isopropyl-1-methanesulfonyl-4-(3'-methanesulfonyl-biphenyl-3-yl)-imidazolidin-2-one,
1-Ethanesulfonyl-3-isopropyl-4-(3'-methanesulfonyl-biphenyl-3-yl)-imidazolidin-2-one,
1-Benzenesulfonyl-4-(4'-hydroxymethyl-3'-methanesulfonyl-bipheny-4-yl)-3-phenyl-imidazolidin-2-one,
1-Benzenesulfonyl-4-(4'-hydroxymethyl-3'-methanesulfonyl-biphenyl-3-yl)-3-isopropyl-imidazolidin-2-one,
1-Benzenesulfonyl-3-isopropyl-4-(3'-nitro-biphenyl-3-yl)-imidazolidin-2-one,
1-Benzenesulfonyl-4-(5'-fluoro-2'-methyl-biphenyl-3-yl)-3-isopropyl-imidazolidin-2-one,
1-Benzenesulfonyl-3-isopropyl-4-[3-(5-methanesulfonyl-pyridin-3-yl)-phenyl]-imidazolidin-2-one,
3'-(1-Benzenesulfonyl-3-isopropyl-2-oxo-imidazolidin-4-yl)-biphenyl-3-sulfonic acid amide,
1-Benzenesulfonyl-4-(2'-chloro-5'-fluoro-biphenyl-3-yl)-3-isopropyl-imidazolidin-2-one,
1-Benzenesulfonyl-4-(5'-chloro-2'-methyl-biphenyl-3-yl)-3-isopropyl-imidazolidin-2-one,
1-Benzenesulfonyl-4-(5'-fluoro-2'-methoxy-biphenyl-3-yl)-3-isopropyl-imidazolidin-2-one,
3'-(1-Benzenesulfonyl-3-isopropyl-2-oxo-imidazolidin-4-yl)-6-chloro-biphenyl-3-carbonitrile,
3'-(1-Benzenesulfonyl-3-isopropyl-2-oxo-imidazolidin-4-yl)-biphenyl-3-sulfonic acid tert-butylamide,
1-Benzenesulfonyl-4-(5'-ethoxy-2'-fluoro-biphenyl-3-yl)-3-isopropyl-imidazolidin-2-one,
1-Benzenesulfonyl-4-(2',5'-dimethyl-biphenyl-3-yl)-3-isopropyl-imidazolidin-2-one,
1-Benzenesulfonyl-4-(2',5'-difluoro-biphenyl-3-yl)-3-isopropyl-imidazolidin-2-one,
4-Benzenesulfonyl-6-(3'-methanesulfonyl-biphenyl-3-yl)-1-phenyl-piperazin-2-one,
4-Benzenesulfonyl-2-(3'-methanesulfonyl-biphenyl-3-yl)-1-phenyl-piperazine,
C-[3'-(4-Benzenesulfonyl-1-phenyl-piperazin-2-yl)-biphenyl-3-yl]-methylamine,
trans-1-Benzenesulfonyl-3-(3'-methanesulfonyl-biphenyl-3-yl)-4-phenyl-piperidine,
trans-[3' (1-Benzenesulfonyl-4-phenyl-piperidin-3-yl)-biphenyl-3-yl]-methylamine,
trans-3-(3'-Methanesulfonyl-biphenyl-3-yl)-4-phenyl-piperidine-1-carboxylic acid tert-butyl ester,
cis-1-Benzenesulfonyl-3-(3'-methanesulfonyl-biphenyl-3-yl)-4-phenyl-piperidine, trans-3-(2',5'-Dimethyl-biphenyl-3-yl)-4-phenyl-piperidine-1-carboxylic acid tert-butyl ester,
cis-3-(2',5'-Dimethyl-biphenyl-3-yl)-4-phenyl-piperidine-1-carboxylic acid tert-butyl ester,
cis-3-(3'-Methanesulfonyl-biphenyl-3-yl)-4-phenyl-piperidine-1-carboxylic acid tert-butyl ester, trans-3-[3-(5-Methanesulfonyl-pyridin-3-yl)-phenyl]-4-phenyl-piperidine-1-carboxylic acid tert-butyl ester,
trans-3-(3'-Methyl-biphenyl-3-yl)-4-phenyl-piperidine-1-carboxylic acid tert-butyl ester,
cis-5-(3'-Methanesulfonyl-biphenyl-3-yl)-2-oxo-4-phenyl-piperidine-1-carboxylic acid tert-butyl ester,
cis-5-[3-(5-Methanesulfonyl-pyridin-3-yl)-phenyl]-2-oxo-4-phenyl-piperidine-1-carboxylic acid tert-butyl ester,
cis-5-(2',5'-Dimethyl-biphenyl-3-yl)-2-oxo-4-phenyl-piperidine-1-carboxylic acid tert-butyl ester,
3-(3'-Methanesulfonyl-biphenyl-3-yl)-4-o-tolyl-piperazine-1-carboxylic acid tert-butyl ester,
3-[3-(5-Methanesulfonyl-pyridin-3-yl)-phenyl]-4-o-tolyl-piperazine-1-carboxylic acid tert-butyl ester, and 4-Benzenesulfonyl-2-(3'-methanesulfonyl-biphenyl-3-yl)-1-o-tolyl-piperazine, and pharmaceutically acceptable salts and esters thereof.

Particularly preferred compounds of formula (I) are those selected from the group consisting of
1-Benzenesulfonyl-4-(3'-methanesulfonyl-biphenyl-3-yl)-3-phenyl-imidazolidin-2-one,
3-Isopropyl-4-(3'-methanesulfonyl-biphenyl-3-yl)-1-(propane-2-sulfonyl)-imidazolidin-2-one,
1-(2-Fluoro-benzenesulfonyl)-3-isopropyl-4-(3'-methanesulfonyl-biphenyl-3-yl)-imidazolidin-2-one
1-Ethanesulfonyl-3-isopropyl-4-(3'-methanesulfonyl-biphenyl-3-yl)-imidazolidin-2-one,
1-Benzenesulfonyl-4-(4'-hydroxymethyl-3'-methanesulfonyl-biphenyl-3-yl)-3-isopropyl-imidazolidin-2-one,
1-Benzenesulfonyl-3-isopropyl-4-[3-(5-methanesulfonyl-pyridin-3-yl)-phenyl]-imidazolidin-2-one,
3'-(1-Benzenesulfonyl-3-isopropyl-2-oxo-imidazolidin-4-yl)-biphenyl-3-sulfonic acid amide,
4-Benzenesulfonyl-2-(3'-methanesulfonyl-biphenyl-3-yl)-1-phenyl-piperazine,
trans-1-Benzenesulfonyl-3-(3'-methanesulfonyl-biphenyl-3-yl)-4-phenyl-piperidine,
trans-[3' (1-Benzenesulfonyl-4-phenyl-piperidin-3-yl)-biphenyl-3-yl]-methylamine,
cis-5-(3'-Methanesulfonyl-biphenyl-3-yl)-2-oxo-4-phenyl-piperidine-1-carboxylic acid tert-butyl ester,
3-(3'-Methanesulfonyl-biphenyl-3-yl)-4-o-tolyl-piperazine-1-carboxylic acid tert-butyl ester, and 4-Benzenesulfonyl-2-(3'-methanesulfonyl-biphenyl-3-yl)-1-o-tolyl-piperazine, and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises reacting a compound of formula (II)

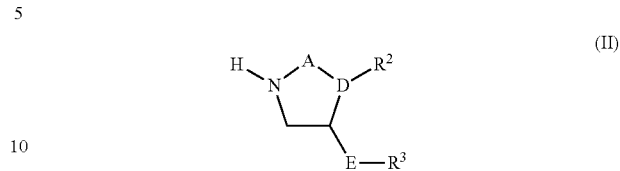

with a compound of formula $R^1$—Cl, wherein $R^1$, $R^2$, $R^3$, A, D and E are as defined above.

The reactions given above can be carried out under conditions well known to the person skilled in the art, e.g. as described below in context with schemes 1, 2, and 3 or in analogy thereto. The present invention also relates to compounds of formula (I) as defined above, when prepared by a process as described above.

The compounds of formula (I) can be prepared by methods known in the art or as described below in schemes 1 to 3. All starting materials are either commercially available, described in the literature or can be prepared by methods well known in the art. Unless otherwise indicated, $R^1$, $R^2$, $R^3$, $R^4$, A, D and E are as described above.

Scheme 1

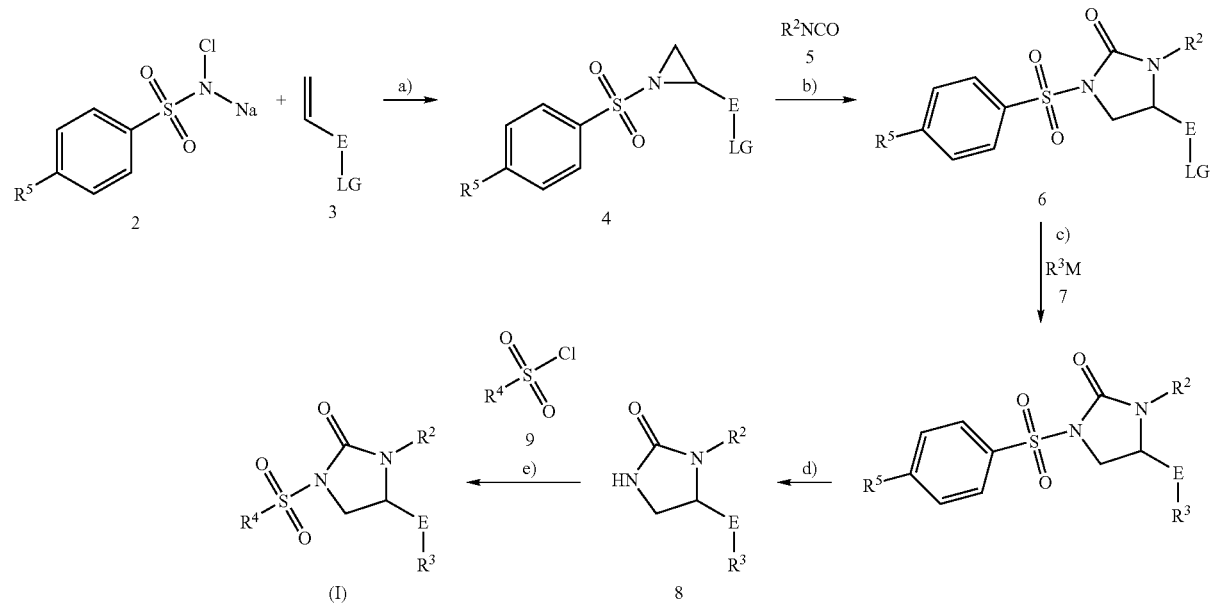

(I) $R^4$ = Ph, 4-CH$_3$Ph
$R^5$ = H, Me
LG = Br, I, Cl, OMs, OTs, OTf
M = B(OH)$_2$, B(OR)$_2$

Compounds of formula (I) can be prepared according to the methods described in scheme 1: Aziridines 4 can be synthesized by reacting chloramine-T (2, $R^5$=Me) or chloramine-B (2, $R^5$=H) with styrene derivatives 3 in the presence of catalysts such as iodine, CuCl or trioctylmethylammonium chloride (Aliquat 336) in a solvent such as acetonitrile, tert-butanol, water, ethanol, phosphate buffer, dimethylformamide or mixtures thereof at temperatures between 0° C. and reflux of the solvent. This type of reactions has been described in *Tetrahedron* 1998, 54, 13485 and *J. Chem. Soc., Perkin Trans.* 1, 2001, 3186 (step a). Treatment of aziridine 4 with an isocyanate 5 (either commercially available or described in the literature or prepared by methods well known to a person skilled in the art) in the presence of a metal halide such as sodium iodide or magnesium bromide in a solvent such as tetrahydrofuran or dioxane at temperatures between 0° C. and room temperature gives the sulfonyl-imidazolidinone 6 (step b). Compounds 6 in which LG represents a leaving group such as Cl, Br, I, OMs, OTs, or OTf can be coupled with suitably substituted aryl or heteroaryl metal species of formula 7, preferably boronic acids or boronic acid esters, such as e.g. boronic acid methyl esters, boronic acid ethylene glycol esters or boronic acid pinacol esters, in the presence of a suitable catalyst, preferably a palladium catalyst such as dichloro[1,1'-bis(diphenylphosphino)ferrocene]palladium (II) or tetrakis(triphenylphosphine)palladium (0) and a base, preferably sodium carbonate, potassium fluoride, potassium carbonate or triethylamine in solvents such as dioxane, water, toluene, N,N-dimethylformamide or mixtures thereof to give compounds of formula (I) in which $R^4$ represents a phenyl or a 4-methylphenyl substituent (step c). The N-arylsulfonyl bond of the N-arylsulfonyl-imidazolidinones obtained in step c can be cleaved under reducing conditions using magnesium in refluxing methanol (see *J. Heterocyclic Chem.* 2004, 41, 737) to give imidazolidinones 8 (step d). Sulfonylation of compounds 8 is achieved with sulfonyl chlorides 9 in solvents such as dimethylacetamide, tetrahydrofuran, dioxane or dichloromethane in the presence of bases such as sodium hydride, N-ethyl-diisopropylamine or triethylamine optionally in the presence of DMAP at 0° C. to room temperature (step e).

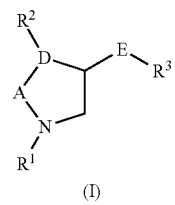

LG = Br, Cl, I, OTf, OTs, OMs
Y = anhydride, Cl
M = B(OH)$_2$, B(OR)$_2$

An alternative synthesis of compounds (I) is depicted in scheme 2. Starting materials 10 are known in literature or can be obtained according to known procedures: piperidine derivatives e.g. to S. Petit, J. P. Nallet, M. Guillard, J. Dreux, R. Chemat, M. Poncelet, C. Bulach, P. Simon, C. Fontaine et al. *European Journal of Medicinal Chemistry* 1991, 26, 19, α-piperidinones in analogy to e.g. W. Barr, J. W. Cook, *J. Chem. Soc.*, 1945, 438 or C. F. Koelsch, R. F. Raffauf, *J. Am. Chem. Soc.* 1944, 66, 1857. For amines the introduction of the residue $R^1 = SO_2R^4$ is achieved by treatment with sulfonyl chlorides 9 in solvents such as dichloromethane, THF, DMF or dioxane with bases such as N-ethyl-diisopropylamine or triethylamine optionally in the presence of DMAP at 0° C. to room temperature (step a). For $R^1$=lower-alkyl-O—C(O), starting material 10 may be converted to compound 12 by treatment with the corresponding lower alkyl dicarbonate 11a in tetrahydrofuran or ether in the presence of N,N-dimethylaminopyridine or with lower alkyl-chloroformates 11b in the presence of a base such as Huenigs base, N-methylmorpholine or triethylamine in dioxane or CH$_2$Cl$_2$. For amides, the introduction of $R^1$ is achieved with sulfonyl chlorides 9, lower alkyl dicarbonates 11a or lower alkyl chloroformates 11b using sodium or potassium hydride, N-ethyl-diisopropylamine or triethylamine in solvents such as dimethylacetamide, tetrahydrofuran, dioxane or dichloromethane at temperatures between 0° C. to reflux. Palladium catalyzed cross-coupling of compound 12 with a suitably substituted aryl or heteroaryl metal species of formula 7, preferably boronic acids or boronic acid esters, such as e.g. boronic acid methyl esters, boronic acid ethylene glycol esters or boronic acid pinacol esters, in the presence of a suitable catalyst, preferably a palladium catalyst such as dichloro[1,1'-bis(diphenylphosphino)ferrocene]palladium (II) or tetrakis-(triphenylphosphine) palladium (0) and a base, preferably sodium carbonate, potassium fluoride, potassium carbonate or triethylamine in solvents such as dioxane, water, 1,2-dimethoxyethane, toluene, N,N-dimethylformamide or mixtures thereof give compounds of formula (I) (step b). If $R^1$ is a protecting moiety such as BOC, the desired residue $R^1$ can be introduced as final step. In this case, the cleavage of the BOC group is achieved with TFA in CH$_2$Cl$_2$ or with HCl in alcohols such as ethanol or methanol. The intermediate amine is then converted to compound (I) by treatment with sulfonyl chlorides 9, lower alkyl dicarbonates 11a or lower alkyl chloroformates 11b as described for step a for amines and with sulfonyl chlorides 9, lower alkyl dicarbonates 11a or lower alkyl chloroformates 11b using sodium or potassium hydride, N-ethyl-diisopropylamine or triethylamine in solvents such as dimethylacetamide, tetrahydrofuran, dioxane or dichloromethane at temperatures between 0° C. to reflux for amides.

If one of the starting materials 7, 9, 10, 11 contains one or more functional groups which are not stable or are reactive under the conditions appropriate protecting groups (as described e.g. in "Protective Groups in Organic Chemistry"

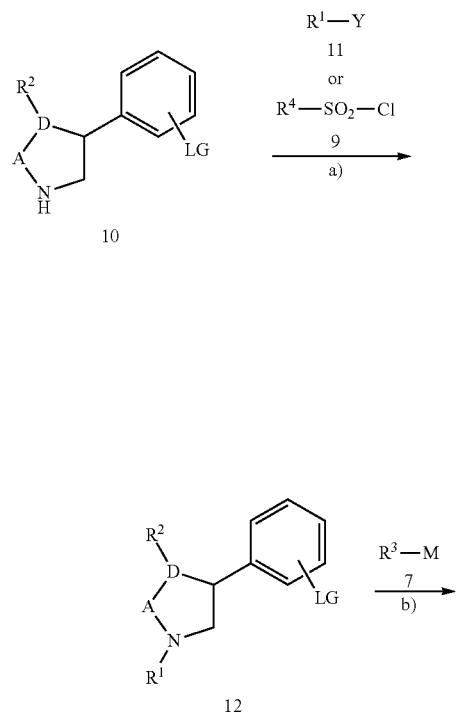

Scheme 2 by T. W. Greene and P. G. M. Wutts, $2^{nd}$ Ed., 1991, Wiley N.Y.) can be introduced before introducing residue $R^1$ or performing the palladium catalyzed cross coupling applying methods well known in the art. Such protecting groups can be removed at a later stage of the synthesis using standard methods described in the literature.

potassium or sodium carbonate (step c). Introduction of the residue $R^1=SO_2R^4$ is achieved by treatment with sulfonyl chlorides 9 in solvents such as dichloromethane, THF, DMF or dioxane with bases such as N-ethyl-diisopropylamine or triethylamine optionally in the presence of DMAP at 0° C. to room temperature (step d). For $R^1$=lower-alkyl-O—C(O),

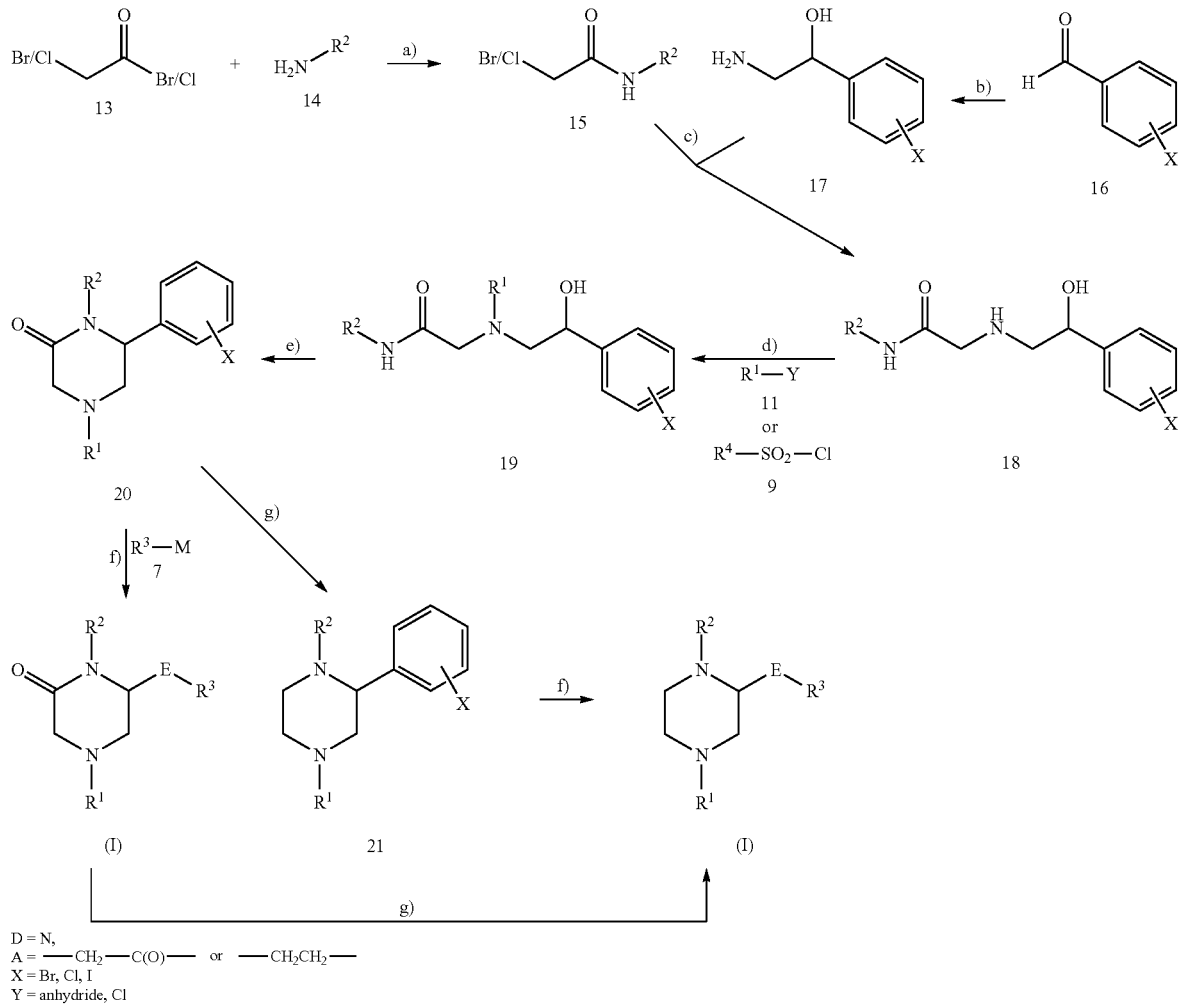

D = N,
A = —CH$_2$—C(O)— or —CH$_2$CH$_2$—
X = Br, Cl, I
Y = anhydride, Cl
M = B(OH)$_2$, B(OR)$_2$ The preparation of derivatives of formula (I) in which A=CH$_2$CH$_2$ or CH$_2$CO and D=N is depicted in scheme 3. The synthesis starts from bromo-acetyl bromide or chloro-acetyl chloride 13 and aminoderivative 14 which are converted to bromo/chloro-acetamide 15 in the presence of bases such as triethylamine, N,N-diisopropylethylamine or N-ethyl morpholine in solvents such as ether, tetrahydrofuran or dichloromethane at room temperature (step a). The second key intermediate 17 can be prepared from aldehyde 16 via cyanohydrins using trimethylsilyl cyanide and bases such as triethylamine, N,N-diisopropylethylamine or N-ethyl morpholine in solvents such as ether, tetrahydrofuran, followed by reduction with reducing agents such as lithium aluminium hydride in THF or ether (step b). Compound 15 can then be converted to the amine 18 with the corresponding aminoalcohol 17 in a suitable solvent such as acetonitrile, THF, DMA, or DMF at RT to reflux in the presence of a base such as amine 18 may be converted to compound 19 by treatment with the corresponding lower alkyl dicarbonate 11a in tetrahydrofuran or ether in the presence of N,N-dimethyl-aminopyridine or with lower alkyl-chloroformates 11b in the presence of a base such as Huenigs base, N-methylmorpholine or triethylamine in dioxane or CH$_2$Cl$_2$. If necessary, the chloroformates may be prepared by reaction of the lower alkyl alcohols with Cl$_3$CCOCl in quinoline. Cyclization to the piperazin-one 20 is achieved by Mitsunobu conditions with triphenylphosphine, diethyl azodicarboxylate (DEAD) or diisopropyl azodicarboxylate (DIAD) in tetrahydrofuran at 0° C. to RT (step e). Palladium catalyzed cross-coupling of compound 20 with a suitably substituted aryl or heteroaryl metal species of formula 7, preferably boronic acids or boronic acid esters, such as e.g. boronic acid methyl esters, boronic acid ethylene glycol esters or boronic acid pinacol esters, in the presence of a suitable catalyst, preferably a palladium catalyst such as dichloro[1,1'-bis(diphenylphosphino)ferrocene]palladium (II) or tetrakis-(triphenylphosphine) palladium (0) and a base, preferably sodium carbonate, potassium fluoride, potassium carbonate or triethylamine in solvents such as dioxane, water, 1,2-dimethoxyethane, toluene, N,N-dimethylformamide or mixtures thereof give compounds of formula (I) (step f). Reduction of compound (I, with A=—CH$_2$—C(O)—) with borane tetrahydrofuran complex in tetrahydrofuran at temperatures between room temperature and reflux yields compound (I, with A=—CH$_2$—CH$_2$—). Alternatively, compound 20 can be reduced to piperazine 21 with borane tetrahydrofuran complex in tetrahydrofuran at temperatures between room temperature and reflux (step g) prior to the palladium catalyzed cross-coupling to compound (I) (step f). If R$^1$ is a protecting moiety such as BOC, the desired residue R$^1$ can be introduced as final step. In this case, the cleavage of the BOC group is achieved with TFA in CH$_2$Cl$_2$ or with HCl in alcohols such as ethanol or methanol. The intermediate amine is then converted to compound (I) by treatment with sulfonyl chlorides 9, lower alkyl dicarbonate 11a or lower alkyl chloroformates 11b as described for step d.

Compounds of the general formula I can contain one or more stereocenters, if no chiral starting materials are used, compounds I can optionally be separated into optically pure enantiomers or diastereomers by methods well known in the art, e.g. by HPLC chromatography, chromatography on a chiral HPLC column, chromatography with a chiral eluant.

The conversion of a compound of formula (I) into a pharmaceutically acceptable salt can be carried out by treatment of such a compound with an inorganic acid, for example a hydrohalic acid, such as, for example, hydrochloric acid or hydrobromic acid, or other inorganic acids such as sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. One method to form such a salt is e.g. by addition of 1/n equivalents of the acid, wherein n=number of acidic protons on the acid, to a solution of the compound in a suitable solvent (e.g. ethanol, ethanol-water mixture, tetrahydrofuran-water mixture) and removal of the solvent by evaporation or lyophilization. If an acidic group is present, the corresponding salts can be prepared from the compounds of formula (I) by treatment with physiologically compatible bases. One possible method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

The conversion of compounds of formula (I) into pharmaceutically acceptable esters can be carried out e.g., by treatment of carboxy groups present in the molecules with a suitable alcohol, with a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluorborate (TPTU) to produce the carboxylic ester. Furthermore, hydroxy groups present in the compounds of formula (I) can be reacted with suitable acids under analogous conditions as described above.

Insofar as their preparation is not described in the examples, the compounds of formula (I) as well as all intermediate products can be prepared according to analogous methods or according to the methods set forth above. Starting materials are commercially available or known in the art.

As described above, the novel compounds of the present invention have been found to bind to and selectively activate LXR alpha and LXR beta or coactivate LXR alpha and LXR beta. Consequently, cholesterol absorption is reduced, HDL cholesterol is increased, and inflammatory atherosclerosis is reduced. They can therefore be used in the treatment and prophylaxis of diseases which are modulated by LXR alpha and/or LXR beta agonists. Such diseases include increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, sepsis, and inflammatory diseases such as colitis, pancreatitis, cholestasis/fibrosis of the liver, psoriasis and other inflammatory diseases of the skin, and diseases that have an inflammatory component such as Alzheimer's disease or impaired/improvable cognitive function. Moreover, the novel compounds of the present invention can be used for treatment of infectious diseases such as HIV as well as cancer and for prophylaxis of age-related and inherited (e.g. Stargardt's disease) forms of macular degeneration.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by LXR alpha and/or LXR beta agonists, particularly as therapeutically active substances for the treatment and/or prophylaxis of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease.

In another preferred embodiment, the invention relates to a method for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease, which method comprises administering a compound as defined above to a human being or animal.

The invention also embraces the use of compounds as defined above for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease.

The invention also relates to the use of compounds as described above for the preparation of medicaments for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease. Such medicaments comprise a compound as described above.

Prevention and/or treatment of increased lipid levels, increased cholesterol levels, atherosclerotic diseases, dyslipidemia, or diabetes is the preferred indication, particularly prevention and/or treatment of increased lipid levels, increased cholesterol levels, atherosclerotic diseases, or dyslipidemia, especially prevention and/or treatment of atherosclerotic diseases or dyslipidemia. Diabetes, particularly non-insulin dependent diabetes mellitus, is another preferred disease.

The following tests were carried out in order to determine the activity of the compounds of the present invention. Background information on the performed assays can be found in: Nichols J S et al. "Development of a scintillation proximity assay for peroxisome proliferator-activated receptor gamma ligand binding domain", Anal Biochem. 1998, 257: 112-119.

Mammalian expression vectors were constructed to express full-length human LXR alpha and LXR beta. Bacterial expression vectors were constructed to produce tagged versions of the ligand binding domains (LBD) of human LXR alpha (aa 164 to 447) and human LXR beta (aa 155 to 460). To accomplish this, the portions of the sequences encoding the LBDs were amplified from the full-length clones by PCR and then subcloned into the plasmid vectors. Final clones were verified by DNA sequence analysis (Willy et al., Genes Dev. 1995, 9:1033-45; Song et al., Proc Natl Acad Sci USA. 1994, 91:10809-13).

Induction, expression, and purification of LBD proteins were performed in *E. coli* strain BL21 (pLysS) cells by standard methods (Ref: Current Protocols in Molecular Biology, Wiley Press, edited by Ausubel et al).

Radioligand Binding Assay

LXR alpha and LXR beta receptor binding were assayed in buffer consisting of 50 mM HEPES, pH 7.4, 10 mM NaCl, 5 mM $MgCl_2$. For each 96-well reaction, 500 ng of LXRα-LBD or 700 ng of LXR beta-LBD proteins were bound to 80 µg or 40 µg SPA beads respectively, in a final volume of 50 µl by shaking. The resulting slurry was incubated for 1 h at RT and centrifuged for 2 min at 1300×g. The supernatant containing unbound protein was removed, and the semi-dry pellet containing the receptor-coated beads was re-suspended in 50 µl of buffer. Radioligand (eg. 100,000 dpm of (N-(2,2,2-trifluoroethyl)-N-[4-(2,2,2-trifluoro-1-hydroxy-1-trifluoromethylethyl)-phenyl]-benzenesulfonamide)) was added, and the reaction incubated at RT for 1 h in the presence of test compounds, and then scintillation proximity counting was performed. All binding assays were performed in 96-well plates and the amount of bound ligand was measured on a Packard TopCount using OptiPlates (Packard). Dose response curves were measured within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% $O_2$:5% $CO_2$ atmosphere. Cells were seeded in 6-well plates at a density of $10^5$ Cells/well and then batch-transfected with either the full-length-LXRα or full-length-LXRβ expression plasmids plus a reporter plasmid expressing luciferase under the control of LXR response elements. Transfection was accomplished with the Fugene 6 reagent (Roche Molecular Biochemicals) according to the suggested protocol. Six hours following transfection, the cells were harvested by trypsinization and seeded in 96-well plates at a density of $10^4$ cells/well. After 24 hours to allow attachment of cells, the medium was removed and replaced with 100 µl of phenol red-free medium containing the test substances or control ligands (final DMSO concentration: 0.1%). Following incubation of the cells for 24 hours with substances, 50 µl of the supernatant was discarded and then 50 µl of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula (I) have an activity in at least one of the above assays (EC50 or IC50) of 1 nM to 100 µM, preferably 1 mM to 10 µM, more preferably 1 nM to 1 µM.

For example, the following compounds showed the following IC50 values in the binding assay:

| Example | LXRalpha Binding IC50 [µmol/l] | LXRbeta Binding IC50 [µmol/l] |
| --- | --- | --- |
| 1 | 11.645 | 2.885 |
| 2 | 7.97 | 8.045 |
| 3 | 10.155 | 5.255 |
| 4 | 1.68 | 0.28 |
| 5 | 4.14 | 5.425 |
| 6 | 5.72 | 9.025 |
| 7 | 0.09 | 0.004 |
| 8 | 0.335 | 0.0745 |
| 9 | 0.425 | 0.36 |
| 10 | 3.35 | 2.69 |
| 11 | 13.03 | 46.14 |
| 12 | 0.1467 | 0.0243 |
| 13 | 2.485 | 0.036 |
| 14 | 0.01 | 0.006 |
| 15 | 2.575 | 0.16 |
| 16 | 0.475 | 0.029 |
| 17 | 52.765 | 2.725 |
| 18 | 5.005 | 0.106 |
| 19 | 0.045 | 0.018 |
| 20 | 0.006 | 0.001 |
| 21 | 2.915 | 0.155 |
| 22 | 4.705 | 1.365 |
| 23 | 2.795 | 0.025 |
| 24 | 0.048 | 0.001 |
| 25 | 2.03 | 0.265 |
| 26 | 1.985 | 0.315 |
| 27 | 6.23 | 3.795 |
| 28 | 2.955 | 0.505 |
| 29 | 2.25 | 0.41 |
| 30 | 0.095 | 0.0104 |
| 31 | 0.815 | 0.165 |
| 32 | 0.95 | 0.0995 |

-continued

| Example | LXRalpha Binding IC50 [μmol/l] | LXRbeta Binding IC50 [μmol/l] |
|---|---|---|
| 33 | 52.745 | 0.53 |
| 34 | 0.056 | 0.002 |
| 35 | 2.62 | 0.425 |
| 36 | 0.07 | 0.025 |
| 37 | 2.54 | 2.09 |
| 38 | 0.16 | 0.025 |
| 39 | 3.03 | 2.75 |
| 40 | 44.065 | 19.305 |
| 41 | 27.445 | 36.775 |
| 42 | 2.825 | 0.61 |
| 43 | 3.98 | 0.755 |
| 44 | 53.685 | 5.51 |
| 45 | 0.24 | 0.021 |
| 46 | 8.215 | 0.385 |
| 47 | 0.185 | 0.22 |
| 48 | 5.525 | 0.355 |
| 49 | 8.88 | 3.745 |
| 50 | 12.325 | 0.165 |

These results have been obtained by using the foregoing test.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-200 mg, of a compound of formula I.

The following examples serve to illustrate the present invention in more detail. They are, however, not intended to limit the scope of the invention in any manner.

EXAMPLES

Example 1

4'-(1-Benzenesulfonyl-2-oxo-3-phenyl-imidazolidin-4-yl)-biphenyl-4-carboxylic acid Step 1: To a stirred suspension of chloramine B (CAS [127-52-6], 1.35 g) in acetonitrile (18 mL) under argon was added iodine (0.16 g). 4-Bromostyrene (2.41 g) was added and the mixture was stirred for 19 h at room temperature. Dichloromethane (240 mL) and water (120 mL) were added and the mixture was extracted with dichloromethane. The org. phase was washed with water and brine, dried over $MgSO_4$ and $K_2CO_3$ and filtered. The filtrate was concentrated and the product was purified using column chromatography ($SiO_2$, cyclohexane/ethyl acetate 95:5=>ethyl acetate) to give 1-benzenesulfonyl-2-(4-bromo-phenyl)-aziridine (1.04 g) as a colorless oil. MS: 340.0 ([M+H]$^+$)

Step 2: To a stirred solution of 1-benzenesulfonyl-2-(4-bromo-phenyl)-aziridine (1.00 g) in tetrahydrofuran (16.5 mL) under argon were added sodium iodide (0.487 g) and phenylisocyanate (0.539 g). The mixture was stirred for 5 days at room temperature. The mixture was diluted with ethyl acetate (50 mL) and washed with water. The org. phase was dried ($MgSO_4$), filtered and concentrated. The product was purified using column chromatography ($SiO_2$, cyclohexane/ethyl acetate 1:0=>0:1) to give 1-benzenesulfonyl-4-(4-bromo-phenyl)-3-phenyl-imidazolidin-2-one (0.974 g) as a colorless solid. MS: 458.9 ([M+H]$^+$)

Step 3: To a stirred solution of 1-benzenesulfonyl-4-(4-bromo-phenyl)-3-phenyl-imidazolidin-2-one (100 mg) and 4-carboxyphenylboronic acid (57 mg) in dioxane (0.6 mL) and water (0.4 mL) under argon were added a 2 M aqueous sodium carbonate solution (0.33 mL) and dichloro[1,1'-bis(diphenylphosphino)ferrocene]palladium dichloromethane adduct (9 mg). The mixture was stirred at 80° C. for 3 h. After cooling to room temperature, the mixture was filtered. The filtrate was diluted with ethyl acetate and washed with 10% aqueous $KHSO_4$ solution. The org. phase was dried ($MgSO_4$), filtered and concentrated. The product was purified using column chromatography ($SiO_2$, dichloromethane/methanol 1:0=>4:1) to give 4'-(1-benzenesulfonyl-2-oxo-3-phenyl-imidazolidin-4-yl)-biphenyl-4-carboxylic acid (36 mg) as an off-white solid. MS: 497.1 ([M-H]$^-$)

Example 2

4'-(1-Benzenesulfonyl-2-oxo-3-phenyl-imidazolidin-4-yl)-biphenyl-3-carboxylic acid In analogy to example 1, step 3,1-benzenesulfonyl-4-(4-bromo-phenyl)-3-phenyl-imidazolidin-2-one (example 1, step 2) was reacted with 3-carboxyphenylboronic acid in the presence of dichloro[1,1'-bis(diphenylphosphino)ferrocene] palladium dichloromethane adduct and sodium carbonate in dioxane/water to give 4'-(1-benzenesulfonyl-2-oxo-3-phenyl-imidazolidin-4-yl)-biphenyl-3-carboxylic acid as an off-white solid. MS: 497.1 ([M−H]$^-$)

Example 3

1-Benzenesulfonyl-4-(2',5'-dimethyl-biphenyl-4-yl)-3-phenyl-imidazolidin-2-one

In analogy to example 1, step 3,1-benzenesulfonyl-4-(4-bromo-phenyl)-3-phenyl-imlidazolidin-2-one (example 1, step 2) was reacted with 2,5-dimethylphenylboronic acid in the presence of dichloro[1,1'-bis(diphenylphosphino)ferrocene]palladium dichloromethane adduct and sodium carbonate in dioxane/water to give 1-benzenesulfonyl-4-(2',5'-dimethyl-biphenyl 4-yl)-3-phenyl-imidazolidin-2-one as a colorless solid. MS: 483.2 ([M+H]$^+$)

Example 4

1-Benzenesulfonyl-4-(3'-methanesulfonyl-biphenyl-4-yl)-3-phenyl-imidazolidin-2-one In analogy to example 1, step 3,1-benzenesulfonyl-4-(4-bromo-phenyl)-3-phenyl-imidazolidin-2-one (example 1, step 2) was reacted with (3-methylsulfonylphenyl)boronic acid in the presence of dichloro[1,1'-bis(diphenylphosphino)ferrocene]palladium dichloromethane adduct and sodium carbonate in dioxane/water to give 1-benzenesulfonyl-4-(3'-methanesulfonyl-biphenyl-4-yl)-3-phenyl-imidazolidin-2-one as an off-white solid. MS: 533.2 ([M+H]$^+$)

Example 5

3'-(1-Benzenesulfonyl-2-oxo-3-phenyl-imidazolidin-4-yl)-biphenyl-4-carboxylic acid Step 1: To a stirred suspension of chloramine B (CAS [127-52-6], 2.97 g), iodine (0.353 g) and trioctylmethylammoniumchloride (Aliquat 336, 0.562 g) in water (40 mL) under argon was added 3-bromostyrene (5.09 g). The mixture was stirred for 2 h at room temperature and subsequently extracted with ethyl acetate. The org. phase was washed with water, dried (MgSO$_4$), filtered and concentrated. The product was purified using column chromatography (SiO$_2$, cyclohexane/ethyl acetate 1:0=>4:1) to give 1-benzenesulfonyl-2-(3-bromo-phenyl)-aziridine (3.18 g) as a light brown oil.

Step 2: In analogy to example 1, step 2,1-benzenesulfonyl-2-(3-bromo-phenyl)-aziridine was reacted with phenylisocyanate and sodium iodide to give 1-benzenesulfonyl-4-(3-bromo-phenyl)-3-phenyl-imidazolidin-2-one as a colorless solid. MS: 459.0 ([M+H]$^+$)

Step 3: In analogy to example 1, step 3,1-benzenesulfonyl-4-(3-bromo-phenyl)-3-phenyl-imidazolidin-2-one was reacted with 4-carboxyphenylboronic acid in the presence of dichloro[1,1'-bis(diphenylphosphino)ferrocene]palladium dichloromethane adduct and sodium carbonate in dioxane/water to give 3'-(1-benzenesulfonyl-2-oxo-3-phenyl-imidazolidin-4-yl)-biphenyl-4-carboxylic acid as an off-white solid. MS: 497.0 ([M−H]$^-$)

Example 6

3'-(1-Benzenesulfonyl-2-oxo-3-phenyl-imidazolidin-4-yl)-biphenyl-3-carboxylic acid In analogy to example 1, step 3,1-benzenesulfonyl-4-(3-bromo-phenyl)-3-phenyl-imidazolidin-2-one (example 5, step 2) was reacted with 3-carboxyphenylboronic acid in the presence of dichloro[1,1'-bis(diphenylphosphino)ferrocene] palladium dichloromethane adduct and sodium carbonate in dioxane/water to give 3'-(1-benzenesulfonyl-2-oxo-3-phenyl-imidazolidin-4-yl)-biphenyl-3-carboxylic acid as an off-white solid. MS: 497.2 ([M−H]$^-$)

Example 7

1-Benzenesulfonyl-4-(3'-methanesulfonyl-biphenyl-3-yl)-3-phenyl-imidazolidin-2-one In analogy to example 1, step 3, 1-benzenesulfonyl-4-(3-bromo-phenyl)-3-phenyl-imidazolidin-2-one (example 5, step 2) was reacted with (3-methylsulfonylphenyl)boronic acid in the presence of dichloro[1,1'-bis(diphenylphosphino)ferrocene]palladium dichloromethane adduct and sodium carbonate in dioxane/water to give 1-benzenesulfonyl-4-(3'-methanesulfonyl-biphenyl-3-yl)-3-phenyl-imidazolidin-2-one as an off-white solid. MS: 533.1 ([M+H]$^+$)

Example 8

N-[3'-(1-Benzenesulfonyl-2-oxo-3-phenyl-imidazolidin-4-yl)-biphenyl-3-yl]-methanesulfonamide In analogy to example 1, step 3,1-benzenesulfonyl-4-(3-bromo-phenyl)-3-phenyl-imidazolidin-2-one (example 5, step 2) was reacted with (3-methylsulfonylaminophenyl)boronic acid in the presence of dichloro[1,1'-bis(diphenylphosphino)ferrocene]palladium dichloromethane adduct and sodium carbonate in dioxane/water to give N-[3'-(1-benzenesulfonyl-2-oxo-3-phenyl-imidazolidin-4-yl)-biphenyl-3-yl]-methanesulfonamide as an off-white solid. MS: 548.2 ([M+H]$^+$)

Example 9

N-[4'-(1-Benzenesulfonyl-2-oxo-3-phenyl-imidazolidin-4-yl)-biphenyl-3-yl]-methanesulfonamide In analogy to example 1, step 3,1-benzenesulfonyl-4-(4-bromo-phenyl)-3-phenyl-imidazolidin-2-one (example 1, step 2) was reacted with (3-methylsulfonylaminophenyl)boronic acid in the presence of dichloro[1,1'-bis(diphenylphosphino)ferrocene]palladium dichloromethane adduct and sodium carbonate in dioxane/water to give N-[4'-(1-benzenesulfonyl-2-oxo-3-phenyl-imidazolidin-4-yl)-biphenyl-3-yl]-methanesulfonamide as a colorless solid. MS: 548.2 ([M+H]$^+$)

Example 10

3-[3'-(1-Benzenesulfonyl-2-oxo-3-phenyl-imidazolidin-4-yl)-biphenyl-4-yl]-propionic acid In analogy to example 1, step 3,1-benzenesulfonyl-4-(3-bromo-phenyl)-3-phenyl-imidazolidin-2-one (example 5, step 2) was reacted with 4-(2-carboxyethyl)benzeneboronic acid in the presence of dichloro[1,1'-bis(diphenylphosphino)

ferrocene]palladium dichloromethane adduct and sodium carbonate in dioxane/water to give 3-[3'-(1-benzenesulfonyl-2-oxo-3-phenyl-imidazolidin-4-yl)-biphenyl-4-yl]-propionic acid as an off-white solid. MS: 525.1 ([M–H]⁻)

Example 11

3'-(1-Benzenesulfonyl-2-oxo-3-phenyl-imidazolidin-4-yl)-biphenyl-2-carboxylic acid In analogy to example 1, step 3,1-benzenesulfonyl-4-(3-bromo-phenyl)-3-phenyl-imidazolidin-2-one (example 5, step 2) was reacted with 2-carboxyphenylboronic acid in the presence of dichloro[1,1'-bis(diphenylphosphino)ferrocene] palladium dichloromethane adduct and sodium carbonate in dioxane/water to give 3'-(1-benzenesulfonyl-2-oxo-3-phenyl-imidazolidin-4-yl)-biphenyl-2-carboxylic acid as an off-white solid. MS: 497.1 ([M–H]⁻)

Example 12

1-Benzenesulfonyl-3-isopropyl-4-(3'-methanesulfonyl-biphenyl-3-yl)-imidazolidin-2-one Step 1: In analogy to example 1, step 2,1-benzenesulfonyl-2-(3-bromo-phenyl)-aziridine (example 5, step 1) was reacted with sodium iodide and isopropyl isocyanate in tetrahydrofuran to give 1-benzenesulfonyl-4-(3-bromo-phenyl)-3-isopropyl-imidazolidin-2-one as a colorless oil.
Step 2: In analogy to example 1, step 3,1-benzenesulfonyl-4-(3-bromo-phenyl)-3-isopropyl-imidazolidin-2-one was reacted with (3-methylsulfonylphenyl)boronic acid in the presence of dichloro[1,1'-bis(diphenylphosphino)ferrocene] palladium dichloromethane adduct and sodium carbonate in dioxane/water to give 1-benzenesulfonyl-3-isopropyl-4-(3'-methanesulfonyl-biphenyl-3-yl)-imidazolidin-2-one as a colorless foam. MS: 499.0 ([M+H]⁺)

Example 13

3-Isopropyl-4-(3'-methanesulfonyl-biphenyl-3-yl)-1-(propane-2-sulfonyl)-imidazolidin-2-one Step 1: 1-Benzenesulfonyl-3-isopropyl-4-(3'-methanesulfonyl-biphenyl-3-yl)-imidazolidin-2-one (example 12, step 2, 1.386 g) and magnesium (0.541 g) were suspended in methanol (30 mL). The mixture was heated to reflux for 4 h and subsequently filtered. The filtrate was concentrated and the product was purified by column chromatography (SiO₂, cyclohexane/ethyl acetate 7:3=>0:1) to give 1-isopropyl-5-(3'-methanesulfonyl-biphenyl-3-yl)-imidazolidin-2-one (0.293 g) as a colorless solid. MS: 359.1 ([M+H]⁺)
Step 2: To a solution of 1-isopropyl-5-(3'-methanesulfonyl-biphenyl-3-yl)-imidazolidin-2-one (40 mg) in N,N-dimethylacetamide (1 mL) under argon at 0° C. was added sodium hydride dispersion (55% in mineral oil, 6 mg). The mixture was stirred at 0° C. for 1.5 h. Isopropylsulfonylchloride (19 mg) was added. The mixture was stirred for 30 min at 0° C. and overnight at room temperature. Ice cold water was added and the mixture was extracted with ethyl acetate. The org. phase was washed with water and concentrated. The product was purified using column chromatography (SiO₂, cyclohexane/ethyl acetate 1:0=>0:1) to give 3-isopropyl-4-(3'-methanesulfonyl-biphenyl-3-yl)-1-(propane-2-sulfonyl)-imidazolidin-2-one (28 mg) as a colorless foam. MS: 465.3 ([M+H]⁺)

Example 14

1-(2-Fluoro-benzenesulfonyl)-3-isopropyl-4-(3'-methanesulfonyl-biphenyl-3-yl)-imidazolidin-2-one In analogy to example 13, step 2,1-isopropyl-5-(3'-methanesulfonyl-biphenyl-3-yl)-imidazolidin-2-one (example 13, step 1) was reacted with sodium hydride and 2-fluorobenzenesulfonyl chloride to give 1-(2-fluoro-benzenesulfonyl)-3-isopropyl-4-(3'-methanesulfonyl-biphenyl-3-yl)-imidazolidin-2-one as a colorless solid. MS: 517.4 ([M+H]⁺)

Example 15

3-Isopropyl-4-(3'-methanesulfonyl-biphenyl-3-yl)-1-(5-methyl-isoxazole-4-sulfonyl)-imidazolidin-2-one In analogy to example 13, step 2,1-isopropyl-5-(3'-methanesulfonyl-biphenyl-3-yl)-imidazolidin-2-one (example 13, step 1) was reacted with sodium hydride and 5-methyl-4-isoxazolesulfonyl chloride to give 3-isopropyl-4-(3'-methanesulfonyl-biphenyl-3-yl)-1-(5-methyl-isoxazole-4-sulfonyl)-imidazolidin-2-one as a light brown solid. MS: 502.4 ([M–H]⁻)

Example 16

1-Benzenesulfonyl-4-(4'-hydroxymethyl-3'-methanesulfonyl-biphenyl-3-yl)-3-phenyl-imidazolidin-2-one To a stirred solution of 1-benzenesulfonyl-4-(3-bromo-phenyl)-3-phenyl-imidazolidin-2-one (example 5, step 2, 129 mg) and 2-methanesulfonyl-4-(4,4,5,5-tetramethyl-[1,3,2]dioxaborolan-2-yl)-phenyl]-methanol (CAS [918328-16-2], 80 mg) in 1,2-dimethoxyethane (2 mL) under argon were added cesium fluoride (87 mg) and tetrakis(triphenylphosphine)palladium(0) (45 mg). The mixture was stirred at 80° C. for 18 h. After cooling to room temperature, water was added and the mixture was extracted with ethyl acetate. The org. phase was washed with brine and concentrated. The product was purified using column chromatography (SiO₂, cyclohexane/ethyl acetate 1:0=>0:1) to give 1-benzenesulfonyl-4-(4'-hydroxymethyl-3'-methanesulfonyl-biphenyl-3-yl)-3-phenyl-imidazolidin-2-one (33 mg) as a colorless solid. MS: 621.3 ([M+OAc]⁻)

Example 17

3-Isopropyl-1-methanesulfonyl-4-(3'-methanesulfonyl-biphenyl-3-yl)-imidazolidin-2-one In analogy to example 13, step 2,1-isopropyl-5-(3'-methanesulfonyl-biphenyl-3-yl)-imidazolidin-2-one (example 13, step 1) was reacted with sodium hydride and methanesulfonyl chloride to give 3-isopropyl-1-methanesulfonyl-4-(3'-methanesulfonyl-biphenyl-3-yl)-imidazolidin-2-one as an off-white solid. MS: 454.4 ([M+NH₄]⁺)

Example 18

1-Ethanesulfonyl-3-isopropyl-4-(3'-methanesulfonyl-biphenyl-3-yl)-imidazolidin-2-one In analogy to example 13, step 2,1-isopropyl-5-(3'-methanesulfonyl-biphenyl-3-yl)-imidazolidin-2-one (example 13, step 1) was reacted with sodium hydride and ethanesulfonyl chloride to give 1-ethanesulfonyl-3-isopropyl-4-(3'-methanesulfonyl-biphenyl-3-yl)-imidazolidin-2-one as a colorless solid. MS: 468.3 ([M+NH$_4$]$^+$)

Example 19

1-Benzenesulfonyl-4-(4'-hydroxymethyl-3'-methanesulfonyl-biphenyl-4-yl)-3-phenyl-imidazolidin-2-one In analogy to example 16, 1-benzenesulfonyl-4-(4-bromophenyl)-3-phenyl-imidazolidin-2-one (example 1, step 2) was reacted with 2-methanesulfonyl-4-(4,4,5,5-tetramethyl-[1,3,2]dioxaborolan-2-yl)-phenyl]-methanol (CAS [918328-16-2]) in 1,2-dimethoxyethane in the presence of cesium fluoride and tetrakis(triphenylphosphine)palladium(0) to give 1-benzenesulfonyl-4-(4'-hydroxymethyl-3'-methanesulfonyl-biphenyl-4-yl)-3-phenyl-imidazolidin-2-one as a colorless solid. MS: 563.3 ([M+H]$^+$)

Example 20

1-Benzenesulfonyl-4-(4'-hydroxymethyl-3'-methanesulfonyl-biphenyl-3-yl)-3-isopropyl-imidazolidin-2-one To a stirred solution of 1-benzenesulfonyl-4-(3-bromophenyl)-3-isopropyl-imidazolidin-2-one (example 12, step 1, 146 mg) and 2-methanesulfonyl-4-(4,4,5,5-tetramethyl-[1,3,2]dioxaborolan-2-yl)-phenyl]-methanol (CAS [918328-16-2], 90 mg) in 1,2-dimethoxyethane (1.5 mL) under argon were added cesium fluoride (88 mg), dichloro[1,1'-bis(diphenylphosphino)ferrocene]palladium dichloromethane adduct (12 mg) and a 1 M aqueous sodium carbonate solution (0.72 mL). The mixture was stirred at 80° C. for 36 h. After cooling to room temperature, water was added and the mixture was extracted with ethyl acetate. The org. phase was washed with water, dried (MgSO$_4$), filtered and concentrated. The product was purified using column chromatography (SiO$_2$, cyclohexane/ethyl acetate 1:0=>0:1) to give 1-benzenesulfonyl-4-(4'-hydroxymethyl-3'-methanesulfonyl-biphenyl-3-yl)-3-isopropyl-imidazolidin-2-one (70 mg) as an off-white solid. MS: 545.9 ([M+NH$_4$]$^+$)

Example 21

1-Benzenesulfonyl-3-isopropyl-4-(3'-nitro-biphenyl-3-yl)-imidazolidin-2-one

In analogy to example 1, step 3,1-benzenesulfonyl-4-(3-bromo-phenyl)-3-isopropyl-imidazolidin-2-one (example 12, step 1) was reacted with (3-nitrophenyl)boronic acid in the presence of dichloro[1,1'-bis(diphenylphosphino)ferrocene]palladium dichloromethane adduct and sodium carbonate in dioxane/water to give 1-benzenesulfonyl-3-isopropyl-4-(3'-nitro-biphenyl-3-yl)-imidazolidin-2-one as a light yellow oil. MS: 466.0 ([M+H]$^+$)

Example 22

1-Benzenesulfonyl-4-(5'-fluoro-2'-methyl-biphenyl-3-yl)-3-isopropyl-imidazolidin-2-one In analogy to example 1, step 3,1-benzenesulfonyl-4-(3-bromo-phenyl)-3-isopropyl-imidazolidin-2-one (example 12, step 1) was reacted with 5-fluoro-2-methylphenylboronic acid in the presence of dichloro[1,1'-bis(diphenylphosphino)ferrocene]palladium dichloromethane adduct and sodium carbonate in dioxane/water to give 1-benzenesulfonyl-4-(5'-fluoro-2'-methyl-biphenyl-3-yl)-3-isopropyl-imidazolidin-2-one as a light yellow oil. MS: 453.1 ([M+H]$^+$)

Example 23

1-Benzenesulfonyl-3-isopropyl-4-[3-(5-methanesulfonyl-pyridin-3-yl)-phenyl]-imidazolidin-2-one In analogy to example 1, step 3,1-benzenesulfonyl-4-(3-bromo-phenyl)-3-isopropyl-imidazolidin-2-one (example 12, step 1) was reacted with 5-(methylsulfonyl)-3-pyridineboronic acid in the presence of dichloro[1,1'-bis(diphenylphosphino)ferrocene]palladium dichloromethane adduct and sodium carbonate in dioxane/water to give 1-benzenesulfonyl-3-isopropyl-4-[3-(5-methanesulfonyl-pyridin-3-yl)-phenyl]-imidazolidin-2-one as a light yellow oil. MS: 499.9 ([M+H]$^+$)

Example 24

3'-(1-Benzenesulfonyl-3-isopropyl-2-oxo-imidazolidin-4-yl)-biphenyl-3-sulfonic acid amide In analogy to example 1, step 3,1-benzenesulfonyl-4-(3-bromo-phenyl)-3-isopropyl-imidazolidin-2-one (example 12, step 1) was reacted with 3-boronobenzenesulfonamide in the presence of dichloro[1,1'-bis(diphenylphosphino)ferrocene]palladium dichloromethane adduct and sodium carbonate in dioxane/water to give 3'-(1-benzenesulfonyl-3-isopropyl-2-oxo-imidazolidin-4-yl)-biphenyl-3-sulfonic acid amide as a colorless solid. MS: 499.9 ([M+H]$^+$)

Example 25

1-Benzenesulfonyl-4-(2'-coro-5'-fluoro-biphenyl-3-yl)-3-isopropyl-imidazolidin-2-one In analogy to example 1, step 3,1-benzenesulfonyl-4-(3-bromo-phenyl)-3-isopropyl-imidazolidin-2-one (example 12, step 1) was reacted with 2-chloro-5-fluorophenylboronic acid in the presence of dichloro[1,1'-bis(diphenylphosphino)ferrocene]palladium dichloromethane adduct and sodium carbonate in dioxane/water to give 1-benzenesulfonyl-4-(2'-chloro-5'-fluoro-biphenyl-3-yl)-3-isopropyl-imidazolidin-2-one as a light yellow oil. MS: 472.9 ([M+H]$^+$)

Example 26

1-Benzenesulfonyl-4-(5'-chloro-2'-methyl-biphenyl-3-yl)-3-isopropyl-imidazolidin-2-one In analogy to example 1, step 3,1-benzenesulfonyl-4-(3-bromo-phenyl)-3-isopropyl-imidazolidin-2-one (example 12, step 1) was reacted with 5-chloro-2-methylphenylboronic acid in the presence of dichloro[1,1'-bis(diphenylphosphino)ferrocene]palladium dichloromethane adduct and sodium carbonate in dioxane/water to give 1-benzenesulfonyl-4-(5'-chloro-2'-methyl-biphenyl-3-yl)-3-isopropyl-imidazolidin-2-one as a light yellow oil. MS: 469.1 ([M+H]$^+$)

Example 27

1-Benzenesulfonyl-4-(5'-fluoro-2'-methoxy-biphenyl-3-yl)-3-isopropyl-imidazolidin-2-one In analogy to example 1, step 3,1-benzenesulfonyl-4-(3-bromo-phenyl)-3-isopropyl-imidazolidin-2-one (example 12, step 1) was reacted with 5-fluoro-2-methoxyphenylboronic acid in the presence of dichloro[1,1'-bis(diphenylphosphino)ferrocene]palladium dichloromethane adduct and sodium carbonate in dioxane/water to give 1-benzenesulfonyl-4-(5'-fluoro-2'-methoxy-biphenyl-3-yl)-3-isopropyl-imidazolidin-2-one as an off-white solid. MS: 469.2 ([M+H]$^+$)

Example 28

3'-(1-Benzenesulfonyl-3-isopropyl-2-oxo-imidazolidin-4-yl)-6-chloro-biphenyl-3-carbonitrile In analogy to example 1, step 3,1-benzenesulfonyl-4-(3-bromo-phenyl)-3-isopropyl-imidazolidin-2-one (example 12, step 1) was reacted with (2-chloro-5-cyanophenyl)boronic acid in the presence of dichloro[1,1'-bis(diphenylphosphino)ferrocene]palladium dichloromethane adduct and sodium carbonate in dioxane/water to give 3'-(1-benzenesulfonyl-3-isopropyl-2-oxo-imidazolidin-4-yl)-6-chloro-biphenyl-3-carbonitrile as a light yellow oil. MS: 480.0 ([M+H]$^+$)

Example 29

3'-(1-Benzenesulfonyl-3-isopropyl-2-oxo-imidazolidin-4-yl)-biphenyl-3-sulfonic acid tert-butylamide In analogy to example 1, step 3,1-benzenesulfonyl-4-(3-bromo-phenyl)-3-isopropyl-imidazolidin-2-one (example 12, step 1) was reacted with 3-tert-butylsulfamoyl-benzeneboronic acid in the presence of dichloro[1,1'-bis(diphenylphosphino)ferrocene]palladium dichloromethane adduct and sodium carbonate in dioxane/water to give 3'-(1-benzenesulfonyl-3-isopropyl-2-oxo-imidazolidin-4-yl)-biphenyl-3-sulfonic acid tert-butylamide as an off-white oil. MS: 572.8 ([M+NH$_4$]$^+$)

Example 30

1-Benzenesulfonyl-4-(5'-ethoxy-2'-fluoro-biphenyl-3-yl)-3-isopropyl-imidazolidin-2-one In analogy to example 1, step 3,1-benzenesulfonyl-4-(3-bromo-phenyl)-3-isopropyl-imidazolidin-2-one (example 12, step 1) was reacted with 5-ethoxy-2-fluorophenylboronic acid in the presence of dichloro[1,1'-bis(diphenylphosphino)ferrocene]palladium dichloromethane adduct and sodium carbonate in dioxane/water to give 1-benzenesulfonyl-4-(5'-ethoxy-2'-fluoro-biphenyl-3-yl)-3-isopropyl-imidazolidin-2-one as a light yellow oil. MS: 483.2 ([M+H]$^+$)

Example 31

1-Benzenesulfonyl-4-(2',5'-dimethyl-biphenyl-3-yl)-3-isopropyl-imidazolidin-2-one In analogy to example 1, step 3,1-benzenesulfonyl-4-(3-bromo-phenyl)-3-isopropyl-imidazolidin-2-one (example 12, step 1) was reacted with 2,5-dimethylphenylboronic acid in the presence of dichloro[1,1-bis(diphenylphosphino)ferrocene]palladium dichloromethane adduct and sodium carbonate in dioxane/water to give 1-benzenesulfonyl-4-(2',5'-dimethyl-biphenyl-3-yl)-3-isopropyl-imidazolidin-2-one as a light yellow oil. MS: 449.2 ([M+H]$^+$)

Example 32

1-Benzenesulfonyl-4-(2',5'-difluoro-biphenyl-3-yl)-3-isopropyl-imidazolidin-2-one In analogy to example 1, step 3,1-benzenesulfonyl-4-(3-bromo-phenyl)-3-isopropyl-imidazolidin-2-one (example 12, step 1) was reacted with 2,5-difluorophenylboronic acid in the presence of dichloro[1,1'-bis(diphenylphosphino)ferrocene]palladium dichloromethane adduct and sodium carbonate in dioxane/water to give 1-benzenesulfonyl-4-(2',5'-difluoro-biphenyl-3-yl)-3-isopropyl-imidazolidin-2-one as a colorless solid. MS: 457.2 ([M+H]$^+$)

Example 33

4-Benzenesulfonyl-6-(3'-methanesulfonyl-biphenyl-3-yl)-1-phenyl-piperazin-2-one

Step 1: To a cooled solution of 3-bromobenzaldehyde (1.58 mL) in THF (15 mL) were added trimethylsilyl cyanide (1.7 mL) and N,N-diisopropylethylamine (0.23 mL). The mixture was stirred at room temperature for 2d and at reflux for 2 h. The solution was allowed to cool to room temperature and then was slowly added to a cooled suspension of lithium aluminium hydride (769 mg) in THF (10 mL). The mixture was stirred at 0° C. for 10 min, the cooling bath was removed, and the mixture was heated at reflux for 3 h. After cooling to room temperature, ethylacetate was added slowly, followed by a mixture of Na$_2$SO$_4$/silicagel/H$_2$O. After stirring the suspension for 30 min, the mixture was filtered, the filtrate was dried (Na$_2$SO$_4$), and concentrated in vacuo. The residue was purified by chromatography (SiO$_2$, CH$_2$Cl$_2$/MeOH/ammonia 90:10:2) to give (1.59 g) 2-amino-1-(3-bromo-phenyl)-ethanol as a yellow oil.

Step 2: At 0° C. to a solution of aniline (2.45 mL) and triethylamine (0.73 mL) in methylene chloride (30 mL) a solution of chloroacetyl chloride (2.56 mL) in methylene chloride (10 mL) was added dropwise. The reaction was stirred at 0° C. for 30 min and then at room temperature for 1 hour. A 1M aqueous solution of KHSO$_4$ was added, the phases were separated and the inorganic one was extracted with ethyl acetate (×3). The combined organic layers were washed with water, brine, dried (Na$_2$SO$_4$) and concentrated in vacuo to yield crude 2-chloro-N-phenyl-acetamide, which was subjected to the next reaction without further purification.

Step 3: To a solution of 2-amino-1-(3-bromo-phenyl)-ethanol (example 33, step 1, 1.34 g) and crude 2-chloro-N-phenyl-acetamide (example 33, step 2, 1.0 g) in acetonitrile (15 mL) was added potassium carbonate (1.03 g). The mixture was heated to 80° C. overnight. A 1M solution of KH$_2$PO$_4$ was added, followed by ethyl acetate. The phases were separated, and the inorganic one was extracted with ethyl acetate (x2). The combined organic layers were washed with brine, dried (Na$_2$SO$_4$) and concentrated in vacuo. Column chromatography (SiO$_2$, CH$_2$Cl$_2$/MeOH 95:5) followed by precipitation from a mixture of diethylether/n-heptane (1:4) gave 2-[2-(3-bromo-phenyl)-2-hydroxy-ethylamino]-N-phenyl-acetamide (0.87 g, 42%) as a white solid, MS: 349.1 (M+H, 1Br)$^+$.

Step 4: To a cooled suspension of 2-[2-(3-bromo-phenyl)-2-hydroxy-ethylamino]-N-phenyl-acetamide (840 mg) and N,N-diisopropylethylamine (760 mL) in methylene chloride (20 mL) was added benzenesulfonyl chloride (0.31 mL). The mixture was stirred at 0° C. for 1 hour and at room temperature overnight. A 1M aqueous solution of KHSO$_4$ was added, the phases were separated, and the inorganic one was extracted with ethyl acetate (×2). The combined organic layers were washed with brine, dried ($Na_2SO_4$) and concentrated in vacuo. The residue was purified by flash chromatography ($SiO_2$, n-heptanelethyl acetate 1:1) to yield 2-{benzenesulfonyl-[2-(3-bromo-phenyl)-2-hydroxy-ethyl]-amino}-N-phenyl-acetamide (1.17 g, 99%) as a white foam, MS: 489.0 (M+H, 1Br)$^+$.

Step 5: At 0° C. to a solution of 2-{benzenesulfonyl-[2-(3-bromo-phenyl)-2-hydroxy-ethyl]-amino}-N-phenyl-acetamide (1.15 g) and triphenylphosphine (678 mg) in ethylacetate (10 mL) was added a solution of diethylazodicarboxylate (0.4 mL) in ethylacetate (5 mL) dropwise. After 15 min. the cooling bath was removed and the mixture was stirred at RT for 3 h. Additional amounts of triphenylphosphine (31 mg) and diethylazodicarboxylate (0.18 mL) were added, and stirring was continued for 1 h. The mixture was diluted with water and ethyl acetate, the phases were separated, and the inorganic one was extracted with ethyl acetate (×2). The organic layers were combined, washed with brine, dried ($Na_2SO_4$) and concentrated in vacuo. The crude product was purified by flash chromatography ($SiO_2$, n-heptane/ethyl acetate 7:3) to give 4-benzenesulfonyl-6-(3-bromo-phenyl)-1-phenyl-piperazin-2-one (0.99 g, 89%) as a white foam, MS: 471.4 (M+H, 1Br)$^+$.

Step 6: To a solution of 4-benzenesulfonyl-6-(3-bromo-phenyl)-1-phenyl-piperazin-2-one (100 mg), (3-methylsulfonylphenyl) boronic acid (46.7 mg) and tetrakis(triphenylphosphine)palladium(0) (24.5 mg) in 1,2-dimethoxyethane (2mL) was added potassium carbonate (73.3 mg). The reaction mixture was stirred at 80° C. overnight. Additional amounts of (3-methylsulfonylphenyl) boronic acid (21 mg), potassium carbonate (58.6 mg) and tetrakis(triphenylphosphine)palladium(0) (24.5 mg) were added and stirring was continued at 80° C. for 3 h. To the reaction mixture water and ethyl acetate were added, the phases were separated, and the inorganic one was extracted with ethyl acetate (×2). The organic layers were combined, washed with brine, dried ($Na_2SO_4$) and concentrated in vacuo. The crude product was purified by column chromatography ($SiO_2$, n-heptane/ethyl acetate 1:3, followed by ISOLUTE Flash $NH_2$, n-heptane/ethyl acetate 1:1) to yield 58 mg (50%) of 4-benzenesulfonyl-6-(3'-methanesulfonyl-biphenyl-3-yl)-1-phenyl-piperazin-2-one as a white foam, MS: 547.3 (M+H)$^+$.

Example 34

4-Benzenesulfonyl-2-(3'-methanesulfonyl-biphenyl-3-yl)-1-phenyl-piperazine

A solution of borane in THF (1M, 274.4 µL) was added to a solution of 4-benzenesulfonyl-6-(3'-methanesulfonyl-biphenyl-3-yl)-1-phenyl-piperazin-2-one (50 mg) in THF (1.5 mL). The reaction mixture was heated to 85° C. for 3 hours. An aqueous solution of $KH_2PO_4$ (1M, 2 mL) was added slowly and the biphasic mixture was heated to 75° C. for 15 min, and then poured into a saturated solution of sodium bicarbonate. Ethyl acetate was added, the phases were separated, and the inorganic one was extracted with ethyl acetate (×2). The organic layers were combined, washed with brine, dried ($Na_2SO_4$) and concentrated in vacuo. Column chromatography ($SiO_2$, n-heptane/ethyl acetate 1:1) yielded 4-benzenesulfonyl-2-(3'-methanesulfonyl-biphenyl-3-yl)-1-phenyl-piperazine (14 mg, 29%) as a white foam, MS: 533.3 (M+H)$^+$.

Example 35

C-[3'-(4-Benzenesulfonyl-1-phenyl-piperazin-2-yl)-biphenyl-3-yl]-methylamine

Step 1: In analogy to example 33, step 6, from 4-benzenesulfonyl-6-(3-bromo-phenyl)-1-phenyl-piperazin-2-one and (3-cyanophenyl)boronic acid was prepared 3'-(4-benzenesulfonyl-6-oxo-1-phenyl-piperazin-2-yl)-biphenyl-3-carbonitrile as a white foam, MS: 494.0 ([M+H]$^+$). Step 2: In analogy to example 34, from 3'-(4-benzenesulfonyl-6-oxo-1-phenyl-piperazin-2-yl)-biphenyl-3-carbonitrile was prepared C—[3'-(4-benzenesulfonyl-1-phenyl-piperazin-2-yl)-biphenyl-3-yl]-methylamine as a white foam, MS: 484.4 ([M+H]$^+$).

Example 36 trans-1-Benzenesulfonyl-3-(3'-methanesulfonyl-biphenyl-3-yl)-4-phenyl-piperidine Step 1: To the hydrochloride salt of rac-trans-3-(m-chlorophenyl)-4-phenylpiperidine (CAS Reg. No.: [134823-41-9]) (500 mg) in methylene chloride (10 mL) triethylamine (677 µL) and benzenesulfonyl chloride (229 µL) were added. The reaction mixture was stirred at room temperature for 4 h, water was added, the phases were separated, and the inorganic one was extracted with ethyl acetate (×3). The organic layers were combined, washed with brine, dried ($Na_2SO_4$) and concentrated in vacuo. Column chromatography ($SiO_2$, n-heptane/ethyl acetate 3:1) yielded trans-1-benzenesulfonyl-3-(3-chloro-phenyl)-4-phenyl-piperidine (0.66 g, 98%) as a white foam, MS: 411 (M, 1 Cl).

Step 2: To a solution of trans-1-benzenesulfonyl-3-(3-chloro-phenyl)-4-phenyl-piperidine (150 mg) and (3-methylsulfonylphenyl)boronic acid (109 mg) in a mixture of DMA/water (2.1 mL, 20:1) was added potassium fluoride (42.3 mg), tetrakis(triphenylphosphine)palladium(0) (50.5 mg) and triphenylphoshine (22.9 mg). The reaction mixture was irradiated with microwave at 160° C. at intervals up to 80 min. Water was added, the phases were separated, and the inorganic one was extracted with diethylether (×2). The organic layers were combined, washed with brine, dried ($Na_2SO_4$) and concentrated in vacuo. Column chromatography ($SiO_2$, n-heptane/ethyl acetate 1:1) yielded trans-1-benzenesulfonyl-3-(3'-methanesulfonyl-biphenyl-3-yl)-4-phenyl-piperidine (51 mg, 26%) as a white foam, MS: 531.5 (M+H)$^+$.

Example 37 trans-[3' (1-Benzenesulfonyl-4-phenyl-piperidin-3-yl)-biphenyl-3-yl]-methylamine Step 1: In analogy to example 36, from trans-1-benzenesulfonyl-3-(3-chloro-phenyl)-4-phenyl-piperidine and 3-(N-Boc)-aminomethylphenylboronic acid was prepared trans-[3'-(1-benzenesulfonyl-4-phenyl-piperidin-3-yl)-biphenyl-3-ylmethyl]-carbamic acid tert-butyl ester as colorless oil, MS: 483.3 (M-$C_4H_9$)$^+$.

Step 2: trans-[3'-(1-Benzenesulfonyl-4-phenyl-piperidin-3-yl)-biphenyl-3-ylmethyl]-carbamic acid tert-butyl ester (10 mg) in ethanol (0.2 mL) was treated with a saturated solution of HCl in ethanol (0.2 mL) for 4 h at room temperature. The solution was evaporated and re-dissolved in an aqueous solution of $NaHCO_3$ and ethyl acetate. The phases were separated and the inorganic one was extracted with ethyl acetate (×2).

The combined organic layers were washed with brine, dried (Na$_2$SO$_4$) and concentrated. Column chromatography (ISOLUTE Flash NH$_2$, n-heptane/ethyl acetate 1:3) yielded trans-[3'(1-benzenesulfonyl-4-phenyl-piperidin-3-yl)-biphenyl-3-yl]-methylamine (7 mg) as colorless oil, MS: 483.5 (M+H)$^+$.

Example 38 trans-3-(3'-Methanesulfonyl-biphenyl-3-yl)-4-phenyl-piperidine-1-carboxylic acid tert-butyl ester Step 1: At 0° C., to a solution of rac-trans-3-(m-chlorophenyl)-4-phenylpiperidine (CAS Reg. No.: [134823-41-9]) in THF (15 mL) di-tert-butyl-dicarbonate (481.8 mg) and 4-dimethylaminopyridine (22.5 mg) were added. The reaction mixture was stirred at RT for 2.5 hours. Additional di-tert-butyl-dicarbonate (200 mg) was added and stirring was continued overnight. A saturated aqueous solution of NaHCO$_3$ was added, the phases were separated and the inorganic one was extracted with ethyl acetate (×2). The combined organic layers were washed with brine, dried (Na$_2$SO$_4$) and concentrated. Column chromatography (ISOLUTE Flash NH$_2$, n-heptane/ethyl acetate 3:1) yielded trans-3-(3-chloro-phenyl)-4-phenyl-piperidine-1-carboxylic acid tert-butyl ester (602 mg, 88%) as colorless oil, MS: 372.0 (M+H, 1Cl)$^+$.

Step 2: To a solution of trans-3-(3-chloro-phenyl)-4-phenyl-piperidine-1-carboxylic acid tert-butyl ester (50 mg) and 3-(methylsulfonyl)phenylboronic acid (40.3 mg) in a mixture of DMA/water (1.1 mL, 10:1) was added Cs$_2$CO$_3$ (87.6 mg) and [(t-Bu)$_2$P(OH)]$_2$PdCl$_2$ (POPd) (8.1 mg). The reaction mixture was irradiated with microwave at 90° C. for 10 min, and at 140° C. for 10 and 15 min. Water was added, the phases were separated, and the inorganic one was extracted with ethyl acetate (×2). The organic layers were combined, washed with brine, dried (Na$_2$SO$_4$) and concentrated in vacuo. Column chromatography (SiO$_2$, n-heptanelethyl acetate 1:1, and on ISOLUTE Flash NH$_2$, n-heptane/ethyl acetate 3:1) yielded trans-3-(3'-methanesulfonyl-biphenyl-3-yl)-4-phenyl-piperidine-1-carboxylic acid tert-butyl ester (33 mg, 49%) as a colorless oil, MS: 509.3 (M+NH$_4$)$^+$.

Example 39 cis-1-Benzenesulfonyl-3-(3'-methanesulfonyl-biphenyl-3-yl)-4-phenyl-piperidine

Step 1: In analogy to Example 38, from rac-cis-3-(m-chlorophenyl)-4-phenylpiperidine (CAS Reg. No.: [735259-16-2]) and benzenesulfonyl chloride was prepared cis-1-benzenesulfonyl-3-(3-chloro-phenyl)-4-phenyl-piperidine as colorless oil, MS: 412.2 (M+H, 1Cl)$^+$.

Step 2: In analogy to Example 38, from cis-1-benzenesulfonyl-3-(3-chloro-phenyl)-4-phenyl-piperidine and (3-methylsulfonylphenyl) boronic acid was prepared cis-1-benzenesulfonyl-3-(3'-methanesulfonyl-biphenyl-3-yl)-4-phenyl-piperidine as a colorless oil, MS: 549.3 (M+NH$_4$)$^+$.

Example 40 trans-3-(2',5'-Dimethyl-biphenyl-3-yl)-4-phenyl-piperidine-1-carboxylic add tert-butyl ester In analogy to example 38, from trans-3-(3-chloro-phenyl)-4-phenyl-piperidine-1-carboxylic acid tert-butyl ester and 2,5-dimethylphenylboronic acid was prepared trans-3-(2',5'-dimethyl-biphenyl-3-yl)-4-phenyl-piperidine-1-carboxylic acid tert-butyl ester as a colorless oil, MS: 442.3 (M+H)$^+$.

Example 41 cis-3-(2',5'-Dimethyl-biphenyl-3-yl)-4-phenyl-piperidine-1-carboxylic acid tert-butyl ester Step 1: In analogy to example 38, from rac-cis-3-(m-chlorophenyl)-4-phenylpiperidine (CAS Reg. No.: [735259-16-2]) and di-tert-butyl-dicarbonate was prepared cis-3-(3-chloro-phenyl)-4-phenyl-piperidine-1-carboxylic acid tert-butyl ester as colorless oil, MS: 372.0 (M+H, 1Cl)$^+$.

Step 2: In analogy to example 38, from cis-3-(3-chloro-phenyl)-4-phenyl-piperidine-1-carboxylic acid tert-butyl ester and 2,5-dimethylphenylboronic acid was prepared cis-3-(2',5'-dimethyl-biphenyl-3-yl)-4-phenyl-piperidine-1-carboxylic acid tert-butyl ester as a colorless oil, MS: 442.3 (M+H)$^+$.

Example 42 cis-3-(3'-Methanesulfonyl-biphenyl-3-yl)-4-phenyl-piperidine-1-carboxylic acid tert-butyl ester In analogy to example 38, from cis-3-(3-chloro-phenyl)-4-phenyl-piperidine-1-carboxylic acid tert-butyl ester and 3-(methylsulfonyl)phenylboronic acid was prepared cis-3-(3'-methanesulfonyl-biphenyl-3-yl)-4-phenyl-piperidine-1-carboxylic acid tert-butyl ester as a colorless oil, MS: 509.2 (M+NH$_4$)$^+$.

Example 43 trans-3-[3-(5-Methanesulfonyl-pyridin-3-yl)-phenyl]-4-phenyl-piperidine-1-carboxylic acid tert-butyl ester In analogy to example 38, from trans-3-(3-chloro-phenyl)-4-phenyl-piperidine-1-carboxylic acid tert-butyl ester and 5-(methylsulfonyl)-3-pyridineboronic acid was prepared trans-3-[3-(5-methanesulfonyl-pyridin-3-yl)-phenyl]-4-phenyl-piperidine-1-carboxylic acid tert-butyl ester as a colorless oil, MS: 493.2 (M+H)$^+$.

Example 44 trans-3-(3'-Methyl-biphenyl-3-yl)-4-phenyl-piperidine-1-carboxylic acid tert-butyl ester In analogy to example 38, from trans-3-(3-chloro-phenyl)-4-phenyl-piperidine-1-carboxylic acid tert-butyl ester and m-tolylboronic acid was prepared trans-3-(3'-methyl-biphenyl-3-yl)-4-phenyl-piperidine-1-carboxylic acid tert-butyl ester as a colorless oil, MS: 428.4 (M+H)$^+$.

Example 45

Cis-5-(3'-Methanesulfonyl-biphenyl-3-yl)-2-oxo-4-phenyl-piperidine-1-carboxylic acid tert-butyl ester Step 1: In analogy to example 38, step 1, from rac cis-5-(3-chloro-phenyl)-4-phenyl-piperidin-2-one (prepared in analogy to W. Barr, J. W. Cook, *J. Chem. Soc.*, 1945, 438) and di-tert-butyl-dicarbonate in presence of 4-dimethylaminopyridine in dichloromethane was prepared cis-5-(3-chloro-phenyl)-2-oxo-4-phenyl-piperidine-1-carboxylic acid tert-butyl ester as a light yellow oil, MS: 386.2 (M+H, 1Cl)$^+$.

Step 2: In analogy to example 38, from cis-5-(3-chloro-phenyl)-2-oxo-4-phenyl-piperidine-1-carboxylic acid tert-butyl ester and 3-(methylsulfonyl)phenylboronic acid was prepared cis-5-(3'-methanesulfonyl-biphenyl-3-yl)-2-oxo-4-phenyl-piperidine-1-carboxylic acid tert-butyl ester as a colorless oil, MS: 406.5 (M+H, —BOC)$^+$.

Example 46 cis-5-[3-(5-Methanesulfonyl-pyridin-3-yl)-phenyl]-2-oxo-4-phenyl-piperidine-1-carboxylic acid tert-butyl ester In analogy to example 38, from cis-5-(3-chloro-phenyl)-2-oxo-4-phenyl-piperidine-1-carboxylic acid tert-butyl ester and 5-(methylsulfonyl)-3-pyridineboronic acid was prepared cis-5-[3-(5-methanesulfonyl-pyridin-3-yl)-phenyl]-2-oxo-4-phenyl-piperidine-1-carboxylic acid tert-butyl ester as a white solid, MS: 507.1 (M+H)$^+$.

Example 47

Cis-5-(2',5'-Dimethyl-biphenyl-3-yl)-2-oxo-4-phenyl-piperidine-1-carboxylic acid tert-butyl ester In analogy to example 38, from cis-5-(3-chloro-phenyl)-2-oxo-4-phenyl-piperidine-1-carboxylic acid tert-butyl ester and 2,5-dimethylphenylboronic acid was prepared cis-5-(2',5'-dimethyl-biphenyl-3-yl)-2-oxo-4-phenyl-piperidine-1-carboxylic acid tert-butyl ester as a colorless oil, MS: 456.4 (M+H)$^+$.

Example 48

3-(3'-Methanesulfonyl-biphenyl-3-yl)-4-o-tolyl-piperazine-1-carboxylic acid tert-butyl ester Step 1: In analogy to example 33 step 2, from o-toluidine and bromoacetyl bromide was prepared 2-bromo-N-o-tolyl-acetamide as crude product, which was directly subjected to the next reaction.

Step 2: In analogy to example 33 step 3, from 2-amino-1-(3-bromo-phenyl)-ethanol (example 33, step 1) and 2-bromo-N-o-tolyl-acetamide was prepared 2-[2-(3-bromo-phenyl)-2-hydroxy-ethylamino]-N-o-tolyl-acetamide as an off-white solid, MS: 363.2 (M+H, 1Br)$^+$.

Step 3: To 2-[2-(3-bromo-phenyl)-2-hydroxy-ethylamino]-N-o-tolyl-acetamide (4 g) in THF (100 mL) was added DMAP (134 mg) and (BOC)$_2$O (2.89 g) in THF (100 mL) at 0° C. The mixture was stirred at room temperature for 2 h. An aqueous solution of NaHCO$_3$ and ethyl acetate was added, the phases were separated and the inorganic one was extracted with ethyl acetate (×2). The combined organic layers were washed with brine, dried (Na$_2$SO$_4$) and concentrated. Column chromatography (SiO$_2$, n-heptane/ethyl acetate 1:1,) yielded [2-(3-bromo-phenyl)-2-hydroxy-ethyl]-(o-tolylcarbamoyl-methyl)-carbamic acid tert-butyl ester (0.88 g, 88%) as a colorless oil, MS: 463.1 (M+H, 1Br)$^+$.

Step 4: In analogy to example 33, step 5, from [2-(3-bromo-phenyl)-2-hydroxy-ethyl]-(o-tolylcarbamoyl-methyl)-carbamic acid tert-butyl ester was prepared 3-(3-bromo-phenyl)-5-oxo-4-o-tolyl-piperazine-1-carboxylic acid tert-butyl ester as a light orange foam, MS: 445.1 (M+H, 1Br)$^+$.

Step 5: In analogy to example 34, from 3-(3-bromo-phenyl)-5-oxo-4-o-tolyl-piperazine-1-carboxylic acid tert-butyl ester was prepared 3-(3-bromo-phenyl)-4-o-tolyl-piperazine-1-carboxylic acid tert-butyl ester as a white foam, MS: 431.2 (M+H, 1Br)$^+$.

Step 6: In analogy to example 33 step 6, from 3-(3-bromo-phenyl)-4-o-tolyl-piperazine-1-carboxylic acid tert-butyl ester and (3-methylsulfonylphenyl)boronic acid was prepared 3-(3'-methanesulfonyl-biphenyl-3-yl)-4-o-tolyl-piperazine-1-carboxylic acid tert-butyl ester as a white foam, MS: 507.1 (M+H)$^+$.

Example 49

3-[3-(5-Methanesulfonyl-pyridin-3-yl)-phenyl]-4-o-tolyl-piperazine-1-carboxylic acid tert-butyl ester In analogy to example 33 step 6, from 3-(3-bromo-phenyl)-4-o-tolyl-piperazine-1-carboxylic acid tert-butyl ester and 5-(methylsulfonyl)-3-pyridineboronic acid was prepared 3-[3-(5-methanesulfonyl-pyridin-3-yl)-phenyl]-4-o-tolyl-piperazine-1-carboxylic acid tert-butyl ester as an orange oil, MS: 508.1 (M+H)$^+$.

Example 50

4-Benzenesulfonyl-2-(3'-methanesulfonyl-biphenyl-3-yl)-1-o-tolyl-piperazine

Step 1: 3-(3'-methanesulfonyl-biphenyl-3-yl)-4-o-tolyl-piperazine-1-carboxylic acid tert-butyl ester (90 mg) in ethanol (1 mL) was treated with a saturated solution of HCl in ethanol (1 mL) at room temperature overnight. The solution was concentrated in vacuo to yield crude 2-(3'-methanesulfonyl-biphenyl-3-yl)-1-o-tolyl-piperazine hydrochloride, MS: 407.3 (M+H)$^+$.

Step 2: To a solution of 2-(3'-methanesulfonyl-biphenyl-3-yl)-1-o-tolyl-piperazine hydrochloride (58 mg) in THF (1 mL) sodium hydride (12.3 mg, 60% in mineral oil) was added. After stirring for 30 min at room temperature, benzenesulfonyl chloride was added at 0° C. and stirring was continued at room temperature overnight. Water and ethyl acetate was added, the phases were separated and the inorganic one was extracted with ethyl acetate (×3). The combined organic layers were washed with water, brine, dried (Na$_2$SO$_4$) and concentrated in vacuo. Column chromatography (SiO$_2$, n-heptane/ethyl acetate 2:1,) yielded 4-benzenesulfonyl-2-(3'-methanesulfonyl-biphenyl-3-yl)-1-o-tolyl-piperazine (55 mg, 42%) as colorless oil, MS: 547.1 (M+H)$^+$.

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |

-continued

| Ingredients | Per tablet | |
|---|---|---|
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 mL |

The active ingredient is dissolved in a mixture of Polyethylene Glycol 400 and water for injection (part). The pH is adjusted to 5.0 by Acetic Acid. The volume is adjusted to 1.0 mL by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:
1. A compound of formula (I)

$$R^1\diagdown_N\diagup^A\diagdown_D\diagup R^2$$
$$\diagdown_{E-R^3}$$

wherein
A is —C(O);
D is N;
E is phenylene which can optionally be substituted with 1 to 4 substituents independently selected from the group consisting of halogen, lower-alkyl and fluoro-lower-alkyl;
$R^1$ is $R^4$—$SO_2$;
$R^2$ is lower-alkyl or aryl, wherein aryl can optionally be substituted with 1 to 4 substituents independently selected from the group consisting of halogen, lower-alkyl, lower-alkoxy, fluoro-lower-alkyl and fluoro-lower-alkoxy;
$R^3$ is phenyl or pyridyl optionally substituted with 1 to 3 substituents independently selected from the group consisting of halogen, lower-alkyl, COOH, lower-alkyl-$SO_2$, lower-alkyl-$SO_2$—NH, COOH-lower-alkyl, hydrox lower-alkyl $NH_2$-lower-alkyl, $NO_2$, CN, $NH_2$—$SO_2$ and N(H,lower-alkyl)-$SO_2$; and
$R^4$ is lower-alkyl, aryl or heteroaryl, wherein aryl or heteroaryl can optionally be substituted with 1 to 4 substituents independently selected from the group consisting of halogen, lower-alkyl, lower-alkoxy, fluoro-lower-alkyl and fluoro-lower-alkoxy;

and pharmaceutically acceptable salts and esters thereof.

2. The compound according to claim 1, wherein E is 1,3-phenylene.

3. The compound according to claim 1, wherein $R^2$ is lower-alkyl or phenyl, which phenyl can optionally be substituted with 1 to 2 substituents independently selected from lower-alkyl.

4. The compound according to claim 3, wherein $R^2$ is isopropyl, phenyl or 2-methyl-phenyl.

5. The compound according to claim 1, wherein $R^3$ is phenyl or pyridinyl optionally substituted with 1 to 2 substituents independently selected from the group consisting of lower-alkyl-$SO_2$, hydroxy-lower-alkyl, $NH_2$-lower-alkyl and $NH_2$—$SO_2$.

6. The compound according to claim 5, wherein $R^3$ is 3-methanesulfonyl-phenyl, 4-hydroxymethyl-3-methanesulfonyl-phenyl, 3-sulfamoyl-phenyl, 5-methanesulfonyl-pyridin-3-yl or 3-aminomehtyl-phenyl.

7. The compound according to claim 1, wherein $R^4$ is lower-alkyl, phenyl or isoxazolyl, which phenyl or isoxazolyl can optionally be substituted with 1 to 2 substituents independently selected from the group consisting of halogen and lower-alkyl.

8. The compound according to claim 7, wherein $R^4$ is lower-alkyl or phenyl, which phenyl can optionally be substituted with halogen.

9. The compound according to claim 8, wherein $R^4$ is ethyl, isopropyl, phenyl or 2-fluoro-phenyl.

10. The compound according to claim 1, selected from the group consisting of
4'-(1-Benzenesulfonyl-2-oxo-3-phenyl-imidazolidin-4-yl)-biphenyl-4-carboxylic acid, 4'-(1-Benzenesulfonyl-2-oxo-3-phenyl-imidazolidin-4-yl)-biphenyl-3-carboxylic acid, 1-Benzenesulfonyl-4-(2',5'-dimethyl-biphenyl-4-yl)-3-phenyl-imidazolidin-2-one, 1-Benzenesulfonyl-4-(3'-methanesulfonyl-biphenyl-4-yl)-3-phenyl-imidazolidin-2-one, 3'-(1-Benzenesulfonyl-2-oxo-3-phenyl-imidazolidin-4-yl)-biphenyl-4-carboxylic acid, 3'-(1-Benzenesulfonyl-2-oxo-3-phenyl-imidazolidin-4-yl)-biphenyl-3-carboxylic acid, 1-Benzenesulfonyl-4-(3'-methanesulfonyl-biphenyl-3-yl)-3-phenyl-imidazolidin-2-one, N-[3'-(1-Benzenesulfonyl-2-oxo-3-phenyl-imidazolidin-4-yl)-biphenyl-3-yl]-methanesulfonamide, N-[4'-(1-Benzenesulfonyl-2-oxo-3-phenyl-imidazolidin-4-yl)-biphenyl-3-yl]-methanesulfonamide, 3-[3'-(1-Benzenesulfonyl-2-oxo-3-phenyl-imidazolidin-4-yl)-biphenyl-4-yl]-propionic acid, and pharmaceutically acceptable salts and esters thereof.

11. A compound according to claim 1, selected from the group consisting of
1-Benzenesulfonyl-4-(3'-methanesulfonyl-biphenyl-3-yl)-3-phenyl-imidazolidin-2-one, 3-Isopropyl-4-(3'-methanesulfonyl-biphenyl-3-yl)-1-(propane-2-sulfonyl)-imidazolidin-2-one,
1-(2-Fluoro-benzenesulfonyl)-3-isopropyl-4-(3'-methanesulfonyl-biphenyl-3-yl)-imidazolidin-2-one 1-Ethanesulfonyl-3-isopropyl-4-(3'-methanesulfonyl-biphenyl-3-yl)-imidazolidin-2-one, 1-Benzenesulfonyl-4-(4'-hydroxymethyl-3'-methanesulfonyl-biphenyl-3-yl)-3-isopropyl-imidazolidin-2-one,
1-Benzenesulfonyl-3-isopropyl-4-[3-(5-methanesulfonyl-pyridin-3-yl)-phenyl]-imidazolidin-2-one,
3'-(1-Benzenesulfonyl-3-isopropyl-2-oxo-imidazolidin-4-yl)-biphenyl-3-sulfonic acid amide, and pharmaceutically acceptable salts and esters thereof.

12. A process for the manufacture of compounds of formula (I) as defined in claim 1, which process comprises reacting a compound of formula (II)

$$\underset{H}{\overset{}{N}}\overset{A}{\underset{}{\diagup}}\overset{D}{\underset{}{\diagdown}}R^2 \atop E-R^3 \qquad (II)$$

with a compound of formula $R^1$—Cl, wherein $R^1$, $R^2$, $R^3$, A, D and E are as defined in claim 1.

13. A pharmaceutical composition comprising a therapeutically effective amount of a compound according to claim 1 and a pharmaceutically acceptable carrier and/or adjuvant.

14. A compound according to claim 1 selected from the group consisting of: 3'-(1-Benzenesulfonyl-2-oxo-3-phenyl-imidazolidin-4-yl)biphenyl-2-carboxylic acid, (RS)-1-Benzenesulfonyl-3-isopropyl-4-(3'-methanesulfonyl-biphenyl-3-yl)-imidazolidin-2-one,
3-Isopropyl-4-(3'-methanesulfonyl-biphenyl-3-yl)-1-(propane-2-sulfonyl)-imidazolidin-2-one,
1-(2-Fluoro-benzenesulfonyl)-3-isopropyl-4-(3'-methanesulfonyl-biphenyl-3-yl)-imidazolidin-2-one,
3-Isopropyl-4-(3'-methanesulfonyl-biphenyl-3-yl)-1-(5-methyl-isoxazole-4-sulfonyl)-imidazolidin-2-one,
1-Benzenesulfonyl-4-(4'-hydroxymethyl-3'-methanesulfonyl-biphenyl-3-yl)-3-phenyl-imidazolidin-2-one,
3-Isopropyl-1-methanesulfonyl-4-(3'-methanesulfonyl-biphenyl-3-yl)-imidazolidin-2-one, 1-Ethanesulfonyl-3-isopropyl-4-(3'-methanesulfonyl-biphenyl-3-yl)-imidazolidin-2-one, 1-Benzenesulfonyl-4-(4'-hydroxymethyl-3'-methanesulfonyl-biphenyl-4-yl)-3-phenyl-imidazolidin-2-one,
1-Benzenesulfonyl-4-(4'-hydroxymethyl-3'-methanesulfonyl-biphenyl-3-yl)-3-isopropyl-imidazolidin-2-one, and pharmaceutically acceptable salts and esters thereof.

15. A compound according to claim 1 selected from the group consisting of: 1-Benzenesulfonyl-3-isopropyl-4-(3'-nitro-biphenyl-3-yl)-imidazolidin-2-one,
1-Benzenesulfonyl-4-(5'-fluoro-2'-methyl-biphenyl-3-yl)-3-isopropyl-imidazolidin-2-one, 1-Benzenesulfonyl-3-isopropyl-4-[3-(5-methanesulfonyl-pyridin-3-yl)-phenyl]-imidazolidin-2-one,
3'-(1-Benzenesulfonyl-3-isopropyl-2-oxo-imidazolidin-4-yl)-biphenyl-3-sulfonic acid amide,
1-Benzenesulfonyl-4-(2'-chloro-5'-fluoro-biphenyl-3-yl)-3-isopropyl-imidazolidin-2-one, 1-Benzenesulfonyl-4-(5'-chloro-2'-methyl-biphenyl-3-yl)-3-isopropyl-imidazolidin-2-one, 1-Benzenesulfonyl-4-(5'-fluoro-2'-methoxy-biphenyl-3-yl)-3-isopropyl-imidazolidin-2-one, 3'-(1-Benzenesulfonyl-3-isopropyl-2-oxo-imidazolidin-4-yl)-6-chloro-biphenyl-3-carbonitrile,
3'-(1-Benzenesulfonyl-3-isopropyl-2-oxo-imidazolidin-4-yl)-biphenyl-3-sulfonic acid tert-butylamide,
1-Benzenesulfonyl-4-(5'-ethoxy-2'-fluoro-biphenyl-3-yl)-3-isopropyl-imidazolidin-2-one, 1-Benzenesulfonyl-4-(2',5'-dimethyl-biphenyl-3-yl)-3-isopropyl-imidazolidin-2-one, 1-Benzenesulfonyl-4-(2',5'-difluoro-biphenyl-3-yl)-3-isopropyl-imidazolidin-2-one, and pharmaceutically acceptable salts and esters thereof.

* * * * *